United States Patent [19]

Carr et al.

[11] Patent Number: 4,892,819
[45] Date of Patent: Jan. 9, 1990

[54] RECOMBINANT DNA EXPRESSION VECTORS AND DNA COMPOUNDS THAT ENCODE ISOPENICILLIN N SYNTHETASE FROM PENICILLIUM CHRYSOGENUM

[75] Inventors: Lucinda G. Carr; Thomas D. Ingolia; Stephen W. Queener, all of Indianapolis; Paul L. Skatrud, Greenwood, all of Ind.

[73] Assignee: Eli Lilly and Company, Indianapolis, Ind.

[21] Appl. No.: 801,523
[22] Filed: Nov. 25, 1985
[51] Int. Cl.$^4$ .................. C12P 21/00; C12P 1/02; C12N 15/00; C12N 9/00
[52] U.S. Cl. ............... 435/69.1; 435/172.3; 435/183; 435/252.3; 435/252.35; 435/254; 435/320; 435/194; 536/27; 935/14; 935/22; 935/34; 935/60; 935/68; 935/72
[58] Field of Search ........ 435/68, 70, 91, 171, 435/172.3, 252.1, 254, 320, 849, 169, 170, 886, 935, 926, 183, 183, 933; 935/6, 22, 27, 36, 60, 68, 73, 61; 536/27

[56] References Cited

U.S. PATENT DOCUMENTS

| | | | |
|---|---|---|---|
| 4,178,210 | 12/1979 | Demain et al. | 435/47 |
| 4,307,192 | 12/1981 | Demain et al. | 435/47 |
| 4,495,287 | 1/1985 | Uhlin et al. | 435/231 |
| 4,618,578 | 10/1986 | Burke et al. | 435/68 |

OTHER PUBLICATIONS

Kaster et al., 1983 NAR II:6895–6911.
Van Solinger et al., 1985, J. Cellular Biochem. Suppl. 9C:174 (Abstr. 1576).
Penalra et al., 1985, J. Cellular Biochem. Suppl. 9C:172 (Abstr. 1570).
Suggs et al., 1981 PNAS 78:66(3–17).
Pang et al., 1984, Biochem. J. 222:789.
Skatrud et al., 1984 Curr Genet 8:155.
Smith et al., 1984 Biochem. Soc. Trans. 12:645.
S. W. Queener and Norbert Neuss, The Chemistry and Biology of β-Lactam Antibiotics, vol. 3, Chapter 1 (1982, Academic Press, Inc.).
Wolfe et al., 1984, Science 226:1386.
Thomas D. Ingolia, a Poster Session at a Meeting of the International Union of Pure & Applied Chemistry, Manchester, England, Sep. 8–13, 1985.
Jerry L. Chapman, Abstract of an Oral Presentation at the 1985 Annual Meeting of the Society for Industrial Microbiology, Boston, Mass., Aug. 3–9, 1985.
Skatrud et al., Abstract of an Oral Presentation Entitled, "The Application of Recombinant DNA Technology to the Antibiotic Producing Filamentous Fungus" Cephalsoporium Acremonium, 4th Annual Toyobo Biotechnology Foundation Symposium Tokyo, Japan, Aug. 30–31, 1985.
Vaara and Vaara, 1983, Nature 303:526.
Ramos et al., 1985, Antimicrobial Agents and Chemotherapy 27(3):380.
Lopez–Nieto et al., 1985, Appl. Microbiol, and Biotechnol. 22:343.
Martin and Liras, 1985, Trends in B iotechnology 3(2):39.
Samson et al., 1985, Nature 318:191.

Primary Examiner—Elizabeth C. Weimar
Assistant Examiner—Richard C. Peet
Attorney, Agent, or Firm—Ron K. Levy; Leroy Whitaker

[57] ABSTRACT

The present invention comprises novel DNA compounds that encode isopenicillin N synthetase. The invention also comprises methods, transformants, and polypeptides related to the novel DNA compounds. The novel isopenicillin N synthetase-encoding DNA, together with its associated transcription and translation activating sequence, was isolated from Penicillium chrysogenum. The isopenicillin N synthetase-encoding DNA can be used to construct novel E. coli expression vectors that drive expression of isopenicillin N synthetase in E. coli. The intact P. chrysogenum isopenicillin N synthetase-encoding DNA and associated transcription and translation activating sequence can also be used to construct expression vectors that drive expression of the isopenicillin N synthetase in P. chrysogenum and Cephalosporium acremonium. The transcription and translation activating sequence can be fused to a hygromycin phosphotransferase-encoding DNA segment and placed onto expression vectors that function in P. chrysogenum and C. acremonium. The transcription termination and mRNA polyadenylation signals of the P. chrysogenum isopenicillin N synthetase can be used to increase ultimate expression of a product encoded on a recombinant DNA vector.

65 Claims, 17 Drawing Sheets

Restriction Site and Function Map of
Plasmid pIT335
(8.24 kb)

Restriction Site and Function Map of
Plasmid pLC2
(7,050 bp)

Restriction Site and Function Map of
Plasmid pCZ106
(10.8 kb)

Restriction Site and Function Map of
Plasmid pLC3
(11.9 kb)

Restriction Site and Function Map of
Plasmid pPS44
(7.9 kb)

Restriction Site and Function Map of
Plasmid pIT221
(8.04 kb)

Restriction Site and Function Map of
Plasmid pPS19
(7.85 kb)

Restriction Site and Function Map of
Plasmid pPS21A
(8.5 kb)

Restriction Site and Function Map of
Plasmid pPS28
(6.6 kb)

Restriction Site and Function Map of
Plasmid pPS29
(6.1 kb)

Restriction Site and Function Map of
Plasmid pPS45A.1
(10.2 kb)

Restriction Site and Function Map of
Plasmid pPS45B.1
(10.2 kb)

Restriction Site and Function Map of
Plasmid pPS42A.1
(9.35 kb)

Restriction Site and Function Map of
Plasmid pPS42B.1
(9.35 kb)

Restriction Site and Function Map of
Plasmid pPS39
(6.6 kb)

Restriction Site and Function Map of
Plasmid pPS41
(3.35 kb)

Restriction Site and Function Map of
Plasmid pPS40
(6.24 kb)

RECOMBINANT DNA EXPRESSION VECTORS AND DNA COMPOUNDS THAT ENCODE ISOPENICILLIN N SYNTHETASE FROM PENICILLIUM CHRYSOGENUM

The present invention comprises a DNA sequence that encodes the isopenicillin N synthetase activity of *Penicillium chrysogenum*. Isopenicillin N synthetase catalyzes the reaction in which isopenicillin N is formed from δ-(L-α-aminoadipyl)-L-cysteinyl-D-valine. This reaction is a critical step in the biosynthesis of important antibiotics such as penicillins from *Penicillium chrysogenum*, *Cephalosporium acremonium*, and *Streptomyces clavuligerus;* cephalosporins from *C. acremonium;* and 7α-methoxycephalosporins from *S. clavuligerus.*

The novel DNA sequence that encodes the isopenicillin N synthetase activity was isolated from *Penicillium chrysogenum* and is useful to construct recombinant DNA expression vectors that drive expression of the activity. Certain vectors of the present invention drive high-level expression of the isopenicillin N synthetase activity in *E. coli*, while others drive expression of the activity in *Cephalosporium acremonium* and *Penicillium chrysogenum*.

The *E. coli*-produced isopenicillin N synthetase activity catalyses the reaction that forms isopenicillin N from δ-(L-α-aminoadipyl)-L-cysteinyl-D-valine. Crude cell extracts from *E. coli* transformed with the *E. coli* vectors of the present invention exhibit isopenicillin N synthetase activity without any prior activation treatment. The *E. coli* vectors of the present invention thus provide an efficient means for obtaining large amounts of active isopenicillin N synthetase. Isopenicillin N synthetase is useful, not only for the production of isopenicillin N, but also for the condensation of tripeptides other than δ-(L-α-aminoadipyl)-L-cysteinyl-D-valine to form novel antibiotics.

The Cephalosporium vectors of the present invention are useful for purposes of strain improvement. Cephalosporium is an economically important organism useful in the production of penicillin and cephalosporin antibiotics. Transformation of Cephalosporium with certain recombinant DNA expression vectors of the present invention will result in higher in vivo levels of isopenicillin N synthetase in the transformants.

Likewise, the Penicillium vectors of the present invention are also useful for purposes of strain improvement. Penicillium is an economically important organism useful in the production of penicillin antibiotics. Transformation of Penicillium with certain recombinant DNA expression vectors of the present invention will result in higher in vivo levels of isopenicillin N synthetase in the transformants. Because the transformants have more isopenicillin N synthetase than their untransformed counterparts, the transformants can produce isopenicillin N more quickly and efficiently and are thus more useful for purposes of producing antibiotic than their untransformed counterparts.

The DNA compounds encoding isopenicillin N synthetase are readily modified to construct expression vectors that increase the efficiency and yield of fermentations involving other organisms, such as *Streptomyces clavuligerus.* Although the isopenicillin N synthetase-encoding DNA of the present invention was isolated from *Penicillium chrysogenum*, the present DNA compounds can be used to construct vectors that drive expression of isopenicillin N synthetase activity in a wide variety of host cells, as the *E. coli* and *Cephalosporium acremonium* vectors of the present invention illustrate. All organisms that produce penicillins and cephalosporins utilize the common precursors δ-(L-α-aminoadipyl)-L-cysteinyl-D-valine and isopenicillin N. Therefore, the isopenicillin N synthetase-encoding DNA compound of the present invention can be used to produce vectors useful for improving efficiency and yield of fermentations involving penicillin and cephalosporin antibiotic-producing organisms of all genera.

The isopenicillin N synthetase-encoding DNA compounds of the present invention were derived from *Penicillium chrysogenum* genomic DNA and were isolated in conjunction with the transcription and translation activating sequence that controls the expression of the isopenicillin N synthetase-encoding genomic DNA. The present invention comprises this novel transcription and translation activating sequence, which can be used to drive expression of genes in *P. chrysogenum* and *Cephalosporium acremonium*.

The present invention also comprises the regulatory signals of the isopenicillin N synthetase gene that are located at the 3' end of the coding strand of the coding region of the gene These 3' regulatory sequences encode the transcription termination and mRNA polyadenylation and processing signals of the gene The presence of these signals in the proper position, which is at the 3' end of the coding strand of the coding region of the gene to be expressed, in an expression vector enhances expression of the desired product encoded by the vector.

The following section provides a more detailed description of the present invention. For purposes of clarity and as an aid in understanding the invention, as disclosed and claimed herein, the following items are defined below.

Antibiotic - a substance produced by a microorganism that, either naturally or with limited chemical modification, will inhibit the growth of or kill another microorganism or eukaryotic cell.

Antibiotic Biosynthetic Gene - a DNA segment that encodes an enzymatic activity that is necessary for an enzymatic reaction in the process of converting primary metabolites into antibiotics.

Antibiotic-Producing Organism - any organism, including, but not limited to, Streptomyces, Bacillus, Monospora, Cephalosporium, Podospora, Penicillium, and Nocardia, that either produces an antibiotic or contains genes produce an antibiotic.

Antibiotic Resistance-Conferring Gene - a DNA segment that encodes an activity that confers resistance to an antibiotic.

ApR - the ampicillin resistance-conferring gene.

bGH - DNA that encodes a bovine growth hormone derivative.

Bifunctional Cloning Shuttle Vector - a recombinant DNA cloning vector which can replicate and/or integrate into organisms of two different taxa.

Ceph DNA - DNA from *Cephalosporium acremonium*

Ceph ori - *Cephalosporium acremonium* mitochondrial DNA that provides for extrachromosomal maintenance of a recombinant DNA vector.

cIPS - isopenicillin N synthetase-encoding DNA of *Cephalosporium acremonium*.

cIPSp - the transcription and translation activating sequence of the isopenicillin N synthetase (IPS) gene of *Cephalosporium acremonium*.

cIPSt - the transcription termination and mRNA polyadenylation and processing signals of the isopenicillin N synthetase gene of *Cephalosporium acremonium.*

Cloning - the process of incorporating a segment of DNA into a recombinant DNA cloning vector.

cos - phage λ cohesive end sequences.

Functional Polypeptide - a recoverable bioactive entirely heterologous or homologous polypeptide or precursor, a recoverable bioactive polypeptide comprising a heterologous polypeptide and a portion or whole of a homologous polypeptide or a recoverable bioinactive fusion polypeptide comprising a heterologous polypeptide and a bioinactivating homologous polypeptide which can be specifically cleaved.

Genomic Library - a set of recombinant DNA cloning vectors into which segments of DNA, which substantially represent the entire genome of a particular organism, have been cloned.

HmR - the hygromycin resistance-conferring gene that confers resistance to hygromycin B.

Hybridization - the process of annealing two homologous single-stranded DNA molecules to form a double-stranded DNA molecule, which may or may not be completely base-paired.

IPS - Isopenicillin N synthetase. Isopenicillin N Synthetase - an enzyme, also known as cyclase, which catalyzes the formation of isopenicillin N from δ-(L-α-aminoadipyl)-L-cysteinyl-D-valine.

kan - the kanamycin resistance-conferring gene.

KmR - the kanamycin resistance-conferring gene.

lacPO - the promoter and operator sequences of the *E. coli* lac operon.

mel - the tyrosinase gene.

mRNA - messenger ribonucleic acid.

ori - an origin of replication that functions in *E. coli.*

Pen DNA - DNA from *Penicillium chrysogenum.*

PGK - the transcription and translation activating sequence of the yeast *Saccharomyces cerevisiae* phosphoglycerate kinase gene.

pIPS - isopenicillin N synthetase-encoding DNA of *Penicillium chrysogenum.* pIPSp - the transcription and translation activating sequence of the isopenicillin N synthetase gene of *Penicillium chrysogenum.* pIPSt - the transcription termination and mRNA polyadenylation and processing signals of the isopenicillin N synthetase gene of *Penicillium chrysogenum.*

Recombinant DNA Cloning Vector - any autonomously replicating or integrating agent, including, but not limited to, plasmids, comprising a DNA molecule to which one or more additional DNA molecules can be or have been added.

Recombinant DNA Expression Vector - any autonomously replicating or integrating agent, including, but not limited to, plasmids, comprising a transcription and translation activating sequence positioned to drive expression of a DNA segment that encodes a polypeptide or RNA of research or commercial interest.

Recombinant DNA Vector - any recombinant DNA cloning or expression vector.

Restriction Fragment - any linear DNA molecule generated by the action of one or more enzymes rRNA - ribosomal ribonucleic acid.

Sensitive Host Cell - a host cell that cannot grow in the presence of a given antibiotic without a DNA segment that confers resistance thereto.

TcR - the tetracycline resistance-conferring gene.

Transcription Activating Sequence - a DNA sequence that promotes transcription of DNA.

Transfectant - a recipient host cell that has undergone transformation by phage DNA.

Transformant - a recipient host cell that has undergone transformation.

Transformation - the introduction of DNA into a recipient host cell that changes the genotype and results in a change in the recipient cell.

Translation Activating Sequence - a DNA sequence that, when translated into mRNA, promotes translation of mRNA into protein.

trp - the transcription and translation activating sequence of the tryptophan operon of *E. coli.*

BRIEF DESCRIPTION OF THE FIGURES

The restriction site and function maps presented in FIGS. 1-17 are approximate representations of the recombinant DNA vectors discussed herein. The spacing of restriction sites on the map is proportional to the actual spacing of the restriction sites on the vector, but observed restriction site distances may vary somewhat from calculated map distances. The restriction site information is not exhaustive; therefore, there may be more restriction sites of a given type on the vector than actually shown on the map.

DETAILED DESCRIPTION OF THE INVENTION

Figure 1:
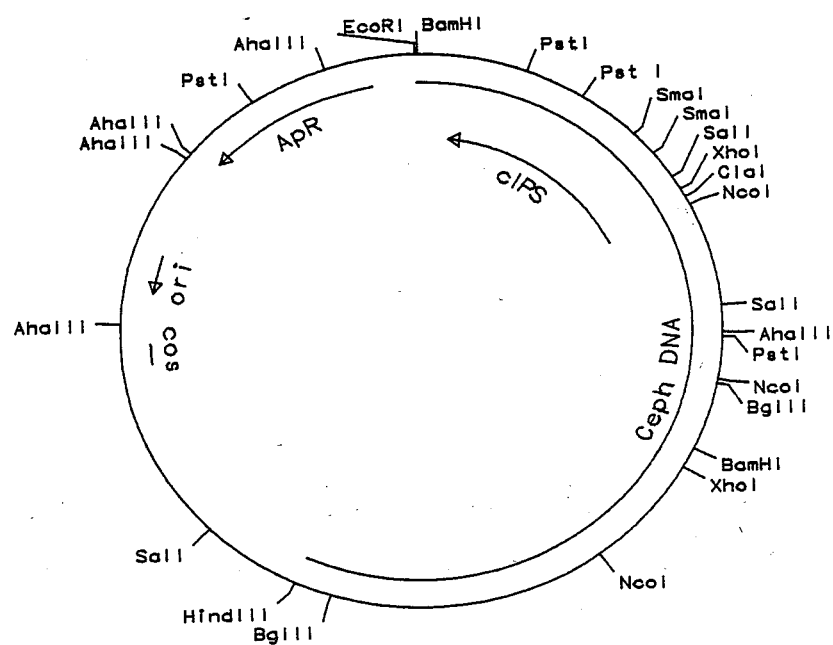
FIG. 1. A restriction site and function map of plasmid pIT335.

The present invention comprises DNA compounds and recombinant DNA cloning and expression vectors that encode the isopenicillin N synthetase activity of *Penicillium chrysogenum*. The sequence of the *P. chrysogenum* isopenicillin N synthetase-encoding DNA is depicted below, together with a portion of the DNA that flanks the 3' end of the coding region in the *P. chrysogenum* genome. In the depiction, only the "sense" or coding strand of the double-stranded DNA molecule is shown, and the DNA is depicted from left to right in the 5'→3'orientation. The nucleotide sequence is numbered; the numbers appear above the DNA sequence.

Immediately below each line of DNA sequence, the amino acid residue sequence of the isopenicillin N synthetase is listed from left to right in the amino-terminus→carboxy-terminus direction. Each amino acid residue appears below the DNA which encodes it. The amino acid residue sequence is numbered; the numbers appear below the amino acid residue sequence.

DNA Sequence Encoding the *Penicillium chrysogenum* Isopenicillin N Synthetase Activity and Corresponding Amino Acid Sequence

| | | | | | | | | | | | | | | | |
|---|---|---|---|---|---|---|---|---|---|---|---|---|---|---|---|
| 5'- ATG<br>MET<br>1 | GCT<br>ALA | TCC<br>SER | ACC<br>THR<br>10 | CCC<br>PRO<br>5 | AAG<br>LYS | GCC<br>ALA | AAT<br>ASN<br>20 | GTC<br>VAL | CCC<br>PRO<br>30<br>10 | AAG<br>LYS | ATC<br>ILE<br>40 | GAC<br>ASP | GTG<br>VAL | TCG<br>SER<br>15 | CCC<br>PRO |
| 50<br>CTG<br>LEU | TTC<br>PHE | GGC<br>GLY | 60<br>GAC<br>ASP<br>20 | AAT<br>ASN | ATG<br>MET | GAG<br>GLU | 70<br>GAG<br>GLU | AAG<br>LYS<br>25 | ATG<br>MET | 80<br>AAG<br>LYS | GTT<br>VAL | GCC<br>ALA | 90<br>CGC<br>ARG<br>30 | GCG<br>ALA | ATT<br>ILE |
| GAC<br>ASP | 100<br>GCT<br>ALA | GCC<br>ALA<br>35 | TCG<br>SER | 110<br>CGC<br>ARG | GAC<br>ASP | ACC<br>THR | 120<br>GGC<br>GLY<br>40 | TTC<br>PHE | TTC<br>PHE | TAC<br>TYR | 130<br>GCG<br>ALA | GTC<br>VAL<br>45 | AAC<br>ASN | 140<br>CAC<br>HIS | GGT<br>GLY |
| GTG<br>VAL | GAT<br>ASP<br>50 | GTG<br>VAL | AAG<br>LYS | CGA<br>ARG | 160<br>CTC<br>LEU | TCG<br>SER<br>55 | AAC<br>ASN | 170<br>AAG<br>LYS | TAC<br>TYR | AGG<br>ARG | 180<br>GAG<br>GLU<br>60 | TTC<br>PHE | CAC<br>HIS | TTT<br>PHE | 190<br>TCT<br>SER |
| ATC<br>ILE<br>65 | ACA<br>THR | 200<br>GAC<br>ASP | GAA<br>GLU | GAG<br>GLU | 210<br>AAG<br>LYS<br>70 | TGG<br>TRP | GAC<br>ASP | CTC<br>LEU | 220<br>GCG<br>ALA | ATT<br>ILE<br>75 | CGC<br>ARG | 230<br>GCC<br>ALA | TAC<br>TYR | AAC<br>ASN | 240<br>AAG<br>LYS<br>80 |
| GAG<br>GLU | CAC<br>HIS | CAG<br>GLN | 250<br>GAC<br>ASP | CAG<br>GLN<br>85 | ATC<br>ILE | 260<br>CGT<br>ARG | GCC<br>ALA | GGA<br>GLY | 270<br>TAC<br>TYR<br>90 | TAC<br>TYR | CTG<br>LEU | TCC<br>SER | 280<br>ATT<br>ILE | CCG<br>PRO<br>95 | GAG<br>GLU |
| 290<br>AAA<br>LYS | AAG<br>LYS | GCC<br>ALA | 300<br>GTG<br>VAL<br>100 | GAA<br>GLU | TCC<br>SER | TTC<br>PHE | 310<br>TGC<br>CYS | TAC<br>TYR<br>105 | CTG<br>LEU | 320<br>AAC<br>ASN | CCC<br>PRO | AAC<br>ASN | 330<br>TTC<br>PHE<br>110 | AAG<br>LYS | CCC<br>PRO |
| GAC<br>ASP | 340<br>CAC<br>HIS | CCT<br>PRO<br>115 | CTC<br>LEU | 350<br>ATC<br>ILE | CAG<br>GLN | TCG<br>SER | 360<br>AAG<br>LYS<br>120 | ACT<br>THR | CCC<br>PRO | ACT<br>THR | 370<br>CAC<br>HIS | GAG<br>GLU<br>125 | GTC<br>VAL | 380<br>AAC<br>ASN | GTG<br>VAL |
| TGG<br>TRP | 390<br>CCG<br>PRO<br>130 | GAC<br>ASP | GAG<br>GLU | AAG<br>LYS | 400<br>AAG<br>LYS | CAT<br>HIS<br>135 | CCG<br>PRO | 410<br>GGC<br>GLY | TTC<br>PHE | CGC<br>ARG | 420<br>GAG<br>GLU<br>140 | TTC<br>PHE | GCC<br>ALA | GAG<br>GLU | 430<br>CAA<br>GLN |
| TAC<br>TYR<br>145 | TAC<br>TYR | 440<br>TGG<br>TRP | GAT<br>ASP | GTG<br>VAL | TTC<br>PHE<br>150 | GGG<br>GLY | CTC<br>LEU | TCG<br>SER | 460<br>TCT<br>SER | GCC<br>ALA<br>155 | TTG<br>LEU | 470<br>CTG<br>LEU | CGA<br>ARG | GGC<br>GLY | TAT<br>TYR<br>160 |
| GCT | CTG | GCG | 490<br>CTG | GGC | AAG | 500<br>GAG | GAG | GAC | 510<br>TTC | TTT | AGC | CGC | 520<br>CAC | TTC | AAG |

DNA Sequence Encoding the *Penicillium chrysogenum* Isopenicillin N Synthetase Activity and Corresponding Amino Acid Sequence -continued

| | | | | | | | | | | | | | | | |
|---|---|---|---|---|---|---|---|---|---|---|---|---|---|---|---|
| ALA | LEU | ALA | LEU | GLY 165 | LYS | GLU | GLU | ASP | PHE 170 | PHE | SER | ARG | HIS | PHE 175 | LYS |
| 530 AAG LYS | GAA GLU | GAC ASP | 540 GCG ALA 180 | CTC LEU | TCC SER | TCG SER | 550 GTT VAL | GTT VAL 185 | CTG LEU | 560 ATT ILE | CGT ARG | TAC TYR | 570 CCG PRO 190 | TAC TYR | CTG LEU |
| AAC ASN | 580 CCC PRO | ATC ILE 195 | CCA PRO | 590 CCT PRO | GCC ALA | GCC ALA | 600 ATT ILE 200 | AAG LYS | ACG THR | GCG ALA | GAC ASP 205 | GGC GLY | GGC GLY | 620 ACC THR | AAA LYS |
| TTG LEU | AGT SER 210 | TTC PHE | GAA GLU | 640 CAT HIS | TGG TRP | GAG GLU 215 | GTG VAL | 650 GTG VAL | TCG SER | ATG MET | ATT ILE 220 | ACC THR | GTC VAL | CTG LEU | 670 TAC TYR |
| CAG GLN 225 | TCA SER | GAC ASP | GTG VAL | GCG ALA | 690 AAC ASN 230 | CTG LEU | CAG GLN | GTG VAL | 700 GAG GLU | ATG MET 235 | CCC PRO | ACC THR | GTC VAL | GGT GLY | 720 CTC LEU 240 |
| GAT ASP | ATC ILE | GAG GLU | 730 GCG ALA | GCG ALA | GAC ASP 245 | TGG TRP | TAC TYR | TAC TYR | 750 CTG LEU 250 | GTC VAL | AAT ASN | TGC CYS | GGC GLY | TAC TYR | TAC TYR |
| 770 ATG MET | GCA ALA | CAC HIS | 780 ATC ILE 260 | ACC THR | AAC ASN | AAC ASN | TAC TYR 265 | TAC TYR | GCT ALA | CCC PRO | ATC ILE | CAC HIS 270 | 810 GTC VAL | GTC VAL | |
| AAG LYS | 820 TGG TRP | GTG VAL 275 | GAT ASP | ACC THR | GAG GLU | CGC ARG | 840 CAA GLN 280 | TCC SER | CTC LEU | CCG PRO | CTC LEU | 850 TTC PHE 285 | TTC PHE | GTC VAL | CTG LEU |
| GGA GLY | TTT PHE 290 | AAT ASN | GAT ASP | 880 GTC VAL | CAG GLN 295 | CAG GLN | CCG PRO | TGG TRP | CCT PRO | 890 AGC SER 300 | AAT ASN | AAG LYS | GAA GLU | GAC ASP | 910 GGC GLY |
| AAG LYS 305 | ACC THR | GAT ASP | 920 CGG ARG | CAG GLN | CCA PRO 310 | ATC ILE | TCG SER | TAC TYR | TAC TYR | TAT TYR | 950 CTG LEU | CAG GLN | AAC ASN | CAG GLN | GGA GLY 320 |
| TTA LEU | GTT VAL | AGT SER | 970 CTA LEU | ATC ILE 325 | AAC ASN | 980 AAG LYS | GGC GLY | GGC GLY | 990 CAG GLN 330 | ACA THR | TAT TYR | AAG | 1000 GGC | CCA | TGG |
| | | | | | | | | | | | TGA | | | | |

DNA Sequence Encoding the *Penicillium chrysogenum* Isopenicillin N Synthetase Activity and Corresponding Amino Acid Sequence -continued

| | | | | 1020 | | | 1030 | | 1040 | | | 1050 | | |
|---|---|---|---|---|---|---|---|---|---|---|---|---|---|---|
| 1010 ATG | GGA | CCG | GGA | TGG | AAA | TCC | CGG | ACT | AGC | TAA | ACC | GAG | TCG | AGA |
| AAA | 1060 AAA | AGG | GAG | 1070 GAG | CCG | CCA | 1080 CCA | TGC | CAC | 1090 CTT | CGT | CTA | 1100 CCT | AAT |
| TAT | 1110 CCA | TAG | CCG | AAG | 1120 GGT | CAA | TAG | 1130 ACC | TCG | 1140 TCG | AAT | AGT | TAT | 1150 TAT |
| TTT | CAC | 1160 CAT | CCA | TGC | CAA | 1170 AAT | GGT | TAA | GCA | TCG | 1190 TTC | CTA | TGT | 1200 GAC |
| CAC | GTA | GAC | 1210 CAT | GCC | AGT | 1220 GAT | TCC | ATG | GCT | TGG | CCC | 1240 GGT | CCA | GTA |
| 1250 GAA | GAC | TGA | 1260 ACC | TCT | TCG | AGA | 1270 TAA | CAA | GAT | 1280 TTT | TCT | TAT | 1290 TGT | AGC |
| ACG | 1300 ATG | GGT | GGG | 1310 GTC | ACC | TCG | TTT | TCT | TCA | 1330 CTG | GCT | CCT | GAA | GAT |
| TTG | 1350 CCT | GGT | AGT | GAG | 1360 CTG | TTT | TAG | GAA | CCA | 1380 GCA | TTG | AAC | TAA | 1390 ATT |
| AGT | ACG | 1400 AAT | CAG | CAG | 1410 AAG | GAC | CAC | GGG | 1420 T—3' | | | | | | wherein A is deoxyadenyl, G is deoxyguanyl, C is deoxycytidyl, T is thymidyl, ALA is an Alanine residue, ARG is an Arginine residue, ASN is an Asparagine residue, ASP is an Aspartic Acid residue, CYS is a Cysteine residue, GLN is a Glutamine residue, GLU is a Glutamic Acid residue, GLY is a Glycine residue, HIS is a Histidine residue, ILE is an Isoleucine residue, LEU is a Leucine residue, LYS is a Lysine residue, MET is a Methionine residue, PHE is a Phenylalanine residue, PRO is a Proline residue, SER is a Serine residue, THR is a Threonine residue, TRP is a Tryptophan residue, TYR is a Tyrosine residue, and VAL is a Valine residue.

Those skilled in the art will recognize that the DNA sequence depicted above is an important part of the present invention. The above sequence can be conventionally synthesized by the modified phosphotriester method using fully protected deoxyribonucleotide building blocks. Such synthetic methods are well known in the art and can be carried out in substantial accordance with the procedure of Itakura et al., 1977, Science 198:1056 and Crea et al., 1978, Proc. Nat. Acad. Sci. U.S.A. 75:575. In addition, an especially preferred method of synthesizing DNA is disclosed in Hsiung et al., 1983, Nucleic Acid Research 11:3227 and Narang et al., 1980, Methods in Enzymology 68:90. In addition to the manual procedures referenced above, the DNA sequence can be synthesized using automated DNA synthesizers, such as the Systec 1450A or ABS 380A DNA Synthesizers.

Due to the degenerate nature of the genetic code, which results from there being more than one codon for most of the amino acid residues and stop signal, the amino acid residue sequence of isopenicillin N synthetase depicted above can be encoded by a multitude of different DNA sequences. Because these alternate DNA sequences would encode the same amino acid residue sequence of the present invention, the present invention further comprises these alternate sequences.

In addition, there could be genetic variants of the isopenicillin N synthetase-encoding DNA of the present invention. These genetic variants would share substantial DNA and amino acid residue sequence homology with the compounds of the present invention and would have similar, if not identical, activity, but would differ somewhat from the actual compounds of the present invention. These genetic variants are equivalent to the compounds of the present invention.

Figure 2:
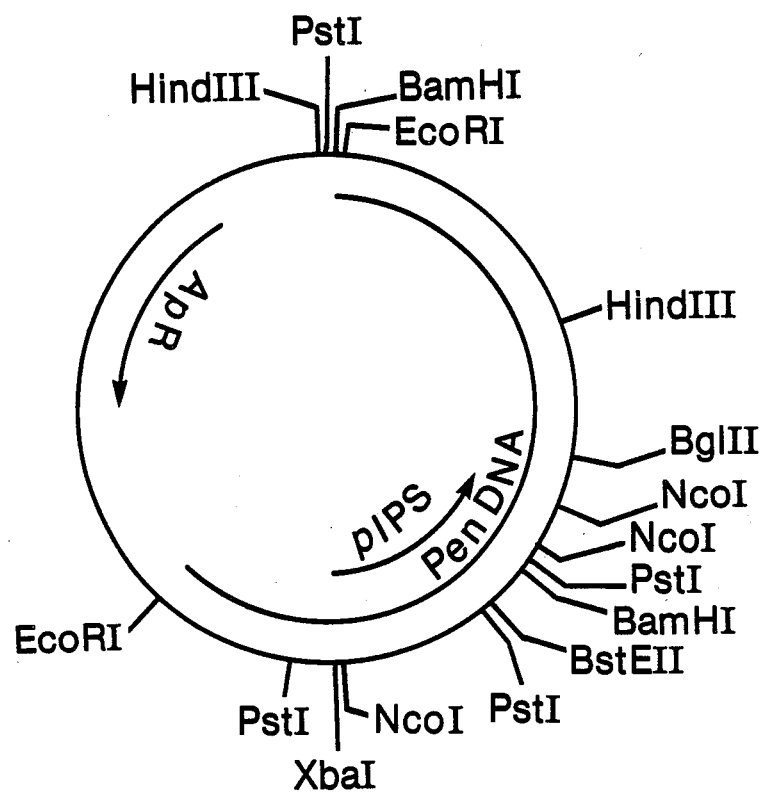
FIG. 2. A restriction site and function map of plasmid pLC2.

The isopenicillin N synthetase activity-encoding DNA compounds of the present invention were isolated from *Penicillium chrysogenum*. A genomic library of the total genomic DNA of the *P. chrysogenum* strain was constructed, and the genomic library was examined for the presence of sequences homologous to the *Cephalosporium acremonium* isopenicillin N synthetase gene encoded on plasmid pIT335, a plasmid available from the Northern Regional Research Laboratories, Agricultural Research Service, U.S. Department of Agriculture, Peoria, Ill., 61604, under the accession No. NRRL B-15960. Plasmid pIT335, a restriction site and function map of which is presented in FIG. 1 of the accompanying drawings, is disclosed and claimed in U.S. patent application Ser. No. 725,870, filed Apr. 22, 1985, attorney docket No. X-6722. A variety of the vectors of the genomic library were identified that were homologous to the *C. acremonium* isopenicillin N synthetase gene, and DNA sequencing revealed that at least one of those vectors encoded the *P. chrysogenum* isopenicillin N synthetase. A derivative of this vector, designated plasmid pLC2, that comprises the complete sequence of the *Penicillium chrysogenum* isopenicillin N synthetase gene has been transformed into *E. coli* K12 JM109 host cells, and the *E. coli* K12 JM109/pLC2 transformants have been deposited and made part of the stock culture collection of the American Type Culture Collection, Rockville, Md., 20852, under the accession number ATCC 53334. A restriction site and function map of plasmid pLC2 is presented in FIG. 2 of the accompanying drawings.

Plasmid pLC2 can be isolated from *E. coli* K12 JM109/pLC2 by the procedure described in Example 1. Plasmid pLC2 was used as starting material in the construction of a plasmid, designated pLC3, that drives high-level expression of isopenicillin N synthetase in *E. coli*. Plasmid pLC3 is constructed by ligating the ~1.6 kb NcoI-BglII restriction fragment of plasmid pLC2 to the ~8.7 kb NcoI-NcoI and ~1.6 kb NcoI-BamHI restriction fragments of plasmid pCZ106.

Figure 3:
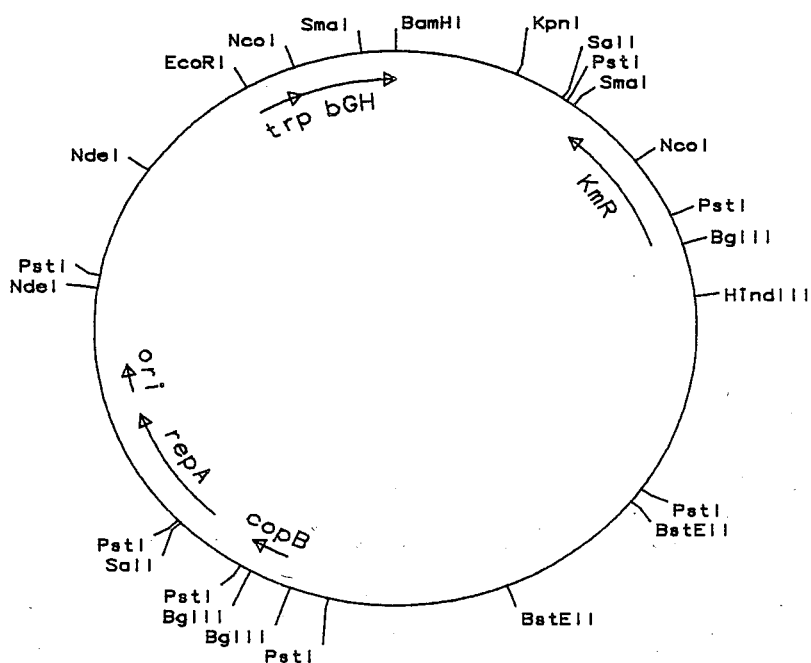
FIG. 3. A restriction site and function map of plasmid pCZ106.

Plasmid pCZ106 comprises a runaway replicon, the trp transcription and translation activating sequence and operator, and a DNA sequence encoding a bovine growth hormone derivative. The use of the type of runaway replicon present on plasmid pCZ106 is described and disclosed in U.S. Pat. Nos. 4,487,835; 4,499,189, and 4,495,287. Essentially, at low temperatures of about 25° C., a plasmid comprising a runaway replicon has a copy number of about ~10–15 copies per *E. coli* host cell, but when the temperature is raised to about 37° C., the copy number increases to about 1,000 copies per *E. coli* host cell. *E. coli* K12 RV308/pCZ106 host cells, from which plasmid pCZ106 can be isolated, have been deposited and made part of the stock culture collection of the Northern Regional Research Laboratories, Peoria, Ill., under the accession number NRRL B-15959. A restriction site and function map of plasmid pCZ106 is presented in FIG. 3 of the accompanying drawings.

Plasmid pLC3 comprises the runaway replicon and trp transcription and translation activating sequence of plasmid pCZ106 and the protein-coding sequence of the isopenicillin N synthetase gene from plasmid pLC2. The ~1.6 kb NcoI-BglII restriction fragment of plasmid pLC2 comprises the entire protein-coding sequence for isopenicillin N synthetase, and the NcoI restriction enzyme recognition sequences; which is

comprises the

Figure 4:
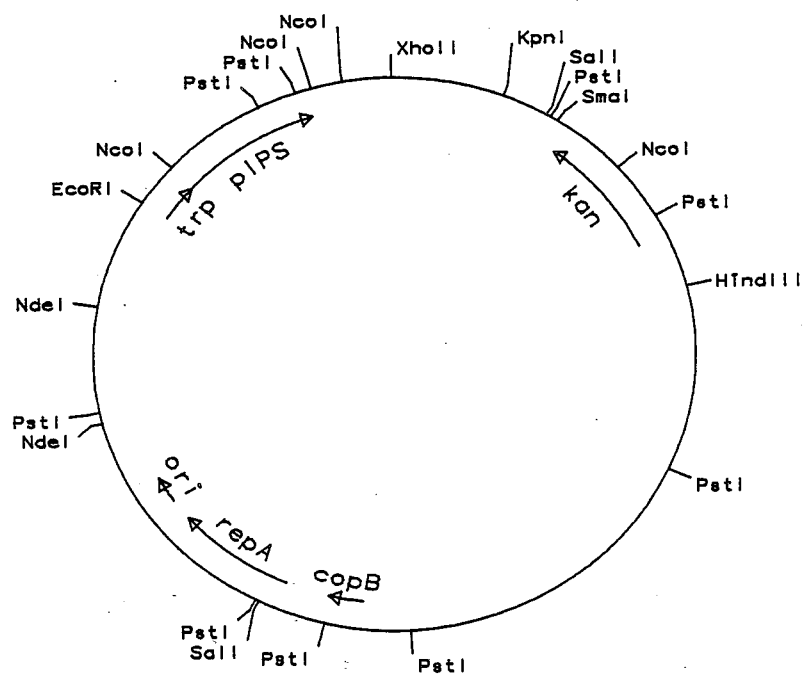
FIG. 4. A restriction site and function map of plasmid pLC3.

that encodes the amino-terminal methionyl residue of isopenicillin N synthetase. The ~1.6 kb NcoI-BglII restriction fragment of plasmid pLC2 also comprises two NcoI restriction sites about 500 bp and 300 bp upstream of the BglII end; consequently, a partial NcoI digest is necessary to isolate the desired fragment. Plasmid pLC3 is constructed so that the trp transcription and translation activating sequence is positioned to drive expression of the isopenicillin N synthetase-encoding DNA. A restriction site and function map of plasmid pLC3 is presented in FIG. 4 of the accompanying drawings. Example 2 describes the construction of plasmid pLC3.

At temperatures of about 37° C., *E. coli* K12 RV308 (NRRL B-15624) cells harboring plasmid pLC3 express isopenicillin N synthetase at high levels, approaching ~10% of the total cell protein. Crude cell extracts from these *E. coli* K12 RV308/pLC3 transformants are able to catalyze the conversion of δ-(L-α-aminoadipyl)-L-cysteinyl-D-valine into isopenicillin N, whereas cell extracts from non-transformed *E. coli* K12 RV308 cells cannot catalyze this conversion. The method of assay for the conversion reaction is presented in Example 3.

Plasmid pLC3 provides an efficient means of producing large amounts of isopenicillin N synthetase in *E. coli*. Because *E. coli* transformants of plasmid pLC3 express isopenicillin N synthetase at levels approaching 10% of total cell protein, and because culturing *E. coli* is less complex than culturing organisms that naturally produce isopenicillin N synthetase, *E. coli*/pLC3 transformants can be used to produce recombinant isopenicillin N synthetase more efficiently and economically than non-recombinant or "natural" isopenicillin N synthetase producers. The *E. coli* K12/pLC3 transformants of the present invention, by producing such high levels of isopenicillin N synthetase, allow for the isolation of the isopenicillin N synthetase encoded on the *Penicillium chrysogenum* genome in substantially pure form.

Isopenicillin N synthetase can be used to produce isopenicillin N from δ-(L-α-aminoadipyl)-L-cysteinyl-D-valine in a cell-free system, as described in Example 3. Isopenicillin N is not only a useful antibiotic, but also is the starting material for the production of such important antibiotics as penicillin N, cephalexin, and other cephalosporins as described in U.S. Pat. No. 4,307,192. Perhaps the most important use of isopenicillin N synthetase is for condensing tripeptides other than δ-(L-α-aminoadipyl)-L-cysteinyl-D-valine into novel β-lactam derivatives.

Cell-free extracts of penicillin-producing organisms can be used to synthesize unnatural (not produced in nature) β-lactams. The *E. coli* expression vectors of the present invention provide an inexpensive and efficient method of obtaining isopenicillin N synthetase, which can be used in vitro to condense tripeptides that do not naturally occur in nature to form novel antibiotics or antibiotic core structures.

The search for unnatural tripeptides that will serve as substrates for isopenicillin N synthetase can be complemented by a search for mutant isopenicillin N synthetases that will accept unnatural tripeptides as substrate. The present invention provides the starting material for such a search for a mutant isopenicillin N synthetase. *E. coli* is the best host for mutational cloning experiments, and the *E. coli* expression vectors of the present invention can be readily mutated by procedures well known in the art, such as, for example, treatment with radiation (X-ray or UV) or chemical mutagens (such as ethylmethanesulfonate, nitrosoguanidine, or methyl methanesulfonate) or site-specific mutagenesis, to obtain mutant enzymes that recognize unnatural tripeptides as substrate and catalyze the condensation of those unnatural tripeptides to unnatural β-lactams Another *E. coli* expression vector of the present invention is constructed by first ligating the ~1.8 kb XmnI restriction fragment of plasmid pKC309 to the ~6.8 kb BstEII-KpnI restriction fragment of plasmid pCZ106 to yield plasmids pIT344 and pIT344.1, which differ only with respect to the orientation of the XmnI restriction fragment. Plasmid pKC309 has been deposited in the permanent culture collection of the Northern Regional Research Center under the accession number NRRL B-15827. Plasmid pKC309 is ~6.8 kb in size, and XmnI digestion of plasmid pKC309 yields three blunt-ended fragments, about 1.6 kb, 1.8 kb, and 3.5 kb in size. The ~1.8 kb XmnI restriction fragment of plasmid pKC309 comprises an apramycin resistance-conferring gene. Plasmid pCZ106 is ~10.9 kb in size, and BstEII and KpnI digestion of plasmid pCZ106 yields three fragments, one ~6.8 kb, one ~0.9 kb, and the other ~3.2 kb in size. The ~6.8 kb BstEII-KpnI restriction fragment of plasmid pCZ106 comprises the trp transcription and translation activating sequence and the runaway replicon. This ~6.8 kb BstEII-KpnI restriction fragment must first be treated with T4 DNA polymerase in the absence of nucleotides to remove the 3' KpnI overlap and then with T4 DNA polymerase in the presence of nucleotides to generate a blunt-ended molecule that will ligate with the ~1.8 kb XmnI restriction fragment of plasmid pCC309 to yield plasmids pIT344 and pIT344.1.

Plasmids pIT344 and pIT344.1 are ~8.4 kb in size, and digestion of both plasmids with restriction enzymes NcoI and BamHI yields restriction fragments of ~7.8 and ~0.6 kb in size. Ligation of the ~7.8 kb NcoI-BamHI restriction fragments of plasmids pIT344 and pIT344.1 to the ~1.6 kb NcoI-BglII restriction fragment of plasmid pLC2 that comprises the complete coding sequence of the isopenicillin N synthetase gene of *Penicillium chrysogenum* respectively yields plasmids pIT345 and pIT345.1. Plasmids pIT345 and pIT345.1 each comprise a runaway replicon, an apramycin resistance-conferring gene, and the trp transcription and translation activating sequence positioned to drive expression of the isopenicillin N synthetase gene of *Penicillium chrysogenum*. *E. coli* K12/pIT345 and *E. coli* K12/pIT345.1 transformants are resistant to 100 μg/ml of apramycin and express isopenicillin N synthetase at levels approaching 10% of the total cellular protein when cultured for four to six hours at 37° C.

The present invention is not limited to the particular vectors exemplified herein. The DNA compounds of the present invention encode the isopenicillin N synthetase activity of *Penicillium chrysogenum* and can be used to isolate homologous DNA compounds from other Penicillium strains that encode genetic variants of the isopenicillin N synthetase of the present invention. Consequently, the present invention comprises DNA compounds homologous to the isopenicillin N synthetase-encoding DNA on plasmid pLC2 that encode isopenicillin N synthetase activity. The DNA compounds of the present invention can be used to construct expression vectors that drive expression of isopenicillin N synthetase in any host cell in which the expression vector replicates or integrates and in which the transcription and translation activating sequence used to express the isopenicillin N synthetase activity functions.

Although the *E. coli* expression vectors that exemplified herein utilize a runaway replicon functions in *E. coli*, the present invention comprises any *E. coli* expression plasmid or vector that drives expression of isopenicillin N synthetase in *E. coli*. Thus, the present invention comprises expression vectors that drive expression of isopenicillin N synthetase and utilize a replicon functional in *E. coli*, such as, for example, a replicon from such plasmids as pBR322, pACYC184, F, ColV-K94, R1, R6-5, or R100. Nor is the present invention solely limited to plasmid vectors, for the present invention also comprises expression vectors that express isopenicillin N synthetase activity and utilize integration or viral replication to provide for replication and maintenance in the host cell.

The present invention is not limited to a particular transcription and translation activating sequence to drive expression of the isopenicillin N synthetase activity-encoding DNA. The present invention comprises the use of any transcription and translation activating sequence to express isopenicillin N synthetase in *E. coli*. Many transcription and translation activating sequences that function in *E. coli* are known and are suitable for driving expression of isopenicillin N synthetase activity in *E. coli*. Such transcription and translation activating sequences include, but are not limited to, the lpp, lac, trp, tac, $\lambda p_L$, and $\lambda p_R$ transcription and translation activating sequences.

In addition to the various *E. coli* transcription and translation activating sequences exemplified above, transcription and translation activating sequences from other organisms can be ligated to the present isopenicillin N synthetase-encoding DNA compounds to form expression vectors that drive expression of isopenicillin N synthetase activity in host cells in which the activating sequence functions. Although *E. coli* is the host best suited for isopenicillin N synthetase production and subsequent purification for in vitro use, vectors that drive expression of isopenicillin N synthetase activity in host cells other than *E. coli* are also useful, especially for purposes of increasing the β-lactam antibiotic-producing ability and efficiency of a given organism.

A variety of organisms produce β-lactam antibiotics. The following Table presents a non-comprehensive list of β-lactam antibiotic-producing organisms.

TABLE I

| β-Lactam Antibiotic-Producing Organisms | |
|---|---|
| Organism | Antibiotic |
| Agrobacterium | various β-lactams |
| Cephalosporium acremonium | penicillins and cephalosporins |
| Chromobacterium | various β-lactams |
| Gluconobacter | various β-lactams |
| Nocardia | |
| lactamdurans | cephamycin C |
| uniformis | nocardicin |
| Penicillium | |
| chrysogenum | various penicillins and other β-lactams |
| Serratia | various β-lactams |
| Streptomyces | |
| antibioticus | clavulanic acid |
| argenteolus | asparenomycin A, MM 4550, and MM 13902 |
| cattleya | thienamycin |
| chartreusis | SF 1623 and cephamycin A and B |
| cinnamonensis | cephamycin A and B |
| clavuligerus | PA-32413-I, cephamycin C, A16886A, penicillins, cephalosporins, clavulanic acid, and other clavams |
| fimbriatus | cephamycin A and B |
| flavovirens | MM 4550 and MM 13902 |
| flavus | MM 4550 and MM 13902 |
| fulvoviridis | MM 4550 and MM 13902 |
| griseus | cephamycin A and B and carpetimycin A and B |
| halstedi | cephamycin A and B |
| heteromorphus | C2081X and cephamycin A and B |

TABLE I-continued

| β-Lactam Antibiotic-Producing Organisms | |
|---|---|
| Organism | Antibiotic |
| hygroscopicus | deacetoxycephalosporin C |
| lipmanii | cephamycin, penicillin N, 7-methoxycephalosporin C, A16884, MM4550, MM13902 |
| olivaceus | epithienamycin F, MM 4550, and MM 13902 |
| panayensis | C2081X and cephamycin A and B |
| pluracidomyceticus | pluracidomycin A |
| rochei | cephamycin A and B |
| sioyaensis | MM 4550 and MM 13902 |
| sp. OA-6129 | OA-6129A |
| sp. KC-6643 | carpetimycin A |
| tokunomensis | asparenomycin A |
| viridochromogenes | cephamycin A and B |
| wadayamensis | WS-3442-D |

Many of the foregoing β-lactam antibiotic-producing organisms are used in the pharmaceutical industry for purposes of antibiotic production. The antibiotic-producing ability of these organisms can be increased and made more efficient by increasing the intracellular concentration of the antibiotic biosynthetic enzymes during the fermentation. The isopenicillin N synthetase activity-encoding DNA compounds of the present invention can be used to construct expression vectors that, when transformed into the appropriate host cell, increase the intracellular concentration of isopenicillin N synthetase activity of the transformed host cell and thereby increase the antibiotic-producing ability and efficiency of that cell, provided that the host cell produces a β-lactam antibiotic via an intermediate reaction involving isopenicillin N synthetase activity.

A vector that will increase the intracellular concentration of isopenicillin N synthetase activity of a given host cell into which the vector is transformed requires the following elements: (1) an isopenicillin N synthetase activity-encoding DNA compound of the present invention; (2) a transcription and translation activating sequence that not only functions in the host cell to be transformed, but also is positioned in the correct orientation and position to drive expression of the isopenicillin N synthetase activity-encoding DNA; and (3) replication or integration functions that provide for maintenance of the vector in the host cell. Of course, the above-described vector could also comprise an antibiotic resistance-conferring gene or some other element that provides a means of selecting for host cells which contain the vector, but such selectable elements may be neither necessary nor desired when the vector integrates into the chromosomal DNA of the host cell.

A variety of the plasmids of the present invention are useful for increasing the intracellular concentration of isopenicillin N synthetase activity in a β-lactam antibiotic-producing cell. Plasmid pLC2 comprises the intact isopenicillin N synthetase gene of *Penicillium chrysogenum*, so transformation of *P. chrysogenum* via chromosomal integration of plasmid pLC2 leads to increased copy number of the isopenicillin N synthetase gene and thus leads to increased intracellular concentration of the enzyme. The *Penicillium chrysogenum* isopenicillin N synthetase gene functions in *Cephalosporium acremonium*. Consequently, transformation of *C. acremonium* via chromosomal integration of plasmid pLC2 leads to increased copy number of the isopenicillin N synthetase gene and thus leads to increased intracellular concentration of the enzyme.

Figure 5:
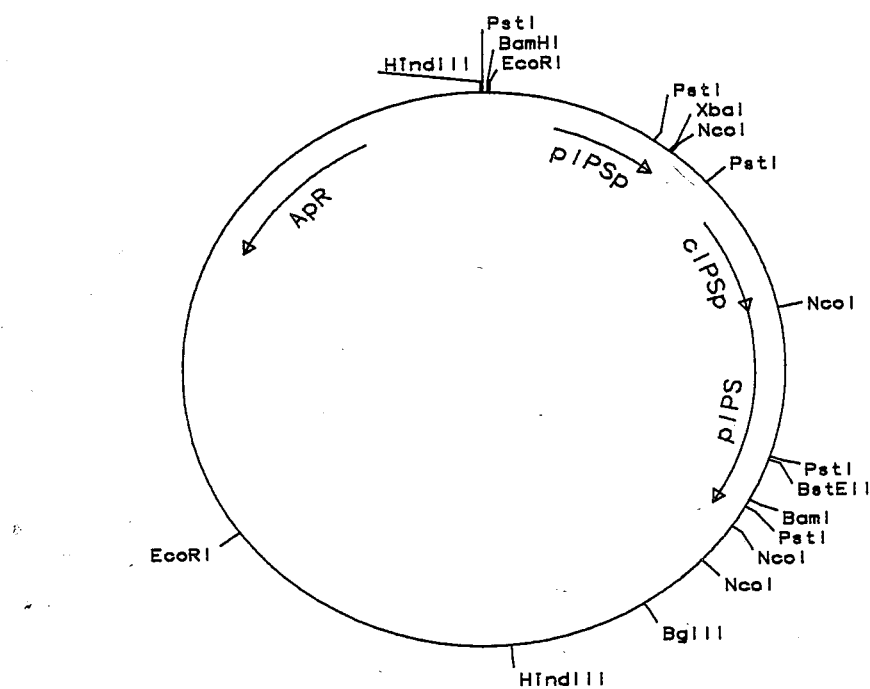
FIG. 5. A restriction site and function map of plasmid pPS44

Plasmid pLC2 can be readily modified to place a homologous *Cephalosporium acremonium* transcription and translation activating sequence in front of the *Penicillium chrysogenum* isopenicillin N synthetase-encoding DNA. The transcription and translation activating sequence of the *C. acremonium* isopenicillin N synthetase gene can be isolated on an ~0.85.kb NcoI restriction fragment from plasmid pIT335 Insertion of this ~0.85 kb NcoI restriction fragment in the proper orientation into the NcoI site located at the 5' end of the coding region of the *P. chrysogenum* isopenicillin N synthetase gene on plasmid pLC2 yields plasmid pPS44, which thus comprises a homologous *C. acremonium* activating sequence positioned to drive expression of the *P. chrysogenum* isopenicillin N synthetase gene. A restriction site and function map of plasmid pPS44 is presented in FIG. 5 of the accompanying drawings, and the construction of plasmid pPS44 is described in Example 4.

The *Cephalosporium acremonium* transcription and translation activating sequence functions in *Penicillium chrysogenum*. Consequently, plasmid pPS44 will increase intracellular levels of isopenicillin N synthetase activity when transformed into either *P. chrysogenum* or *C. acremonium*. Plasmid pPS44 does not comprise a selectable marker that functions in either *P. chrysogenum* or *C. acremonium* but can be readily modified to comprise such a marker. Ingolia et al., U.S. patent application Ser. No. 895,008, Attorney Docket No. X-6722B, which is a continuation-in-part U.S. patent application Ser. No. 799,384, Attorney Docket No. X-6722A, now abandoned, a continuation-in-part application of U.S. patent application Ser. No. 725,870, filed Apr. 22, 1985, describes a plasmid, designated pPS29, that comprises the transcription and translation activating sequence of the *C. acremonium* isopenicillin N synthetase gene positioned to drive expression of a hygromycin resistance-conferring gene.

Figure 10:
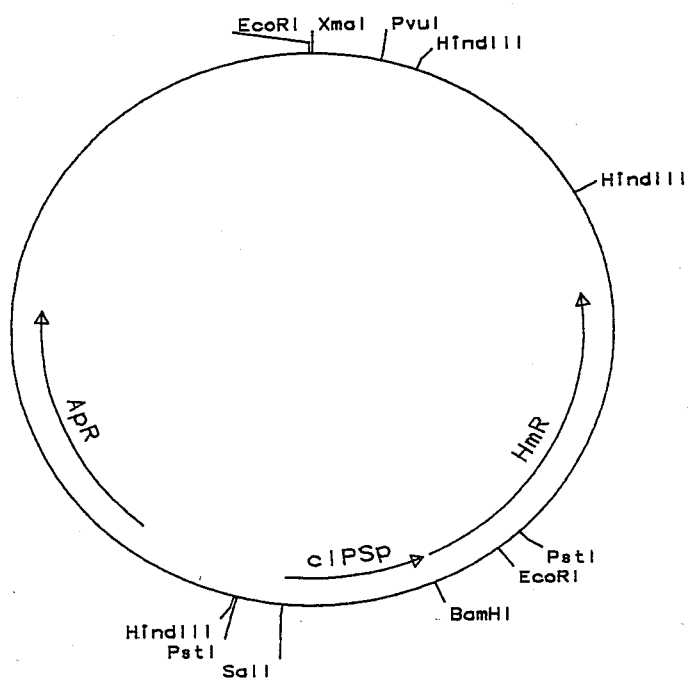
FIG. 10. A restriction site and function map of plasmid pPS29.

The hygromycin resistance-conferring gene on plasmid pPS29 can be used as a selectable marker in both *Cephalosporium acremonium* and *Penicillium chrysogenum*, as described in Chapman et al., U.S. patent application Ser. No. 654,919. Attorney Docket No. X-6570, filed Sept. 27, 1984. This selectable marker can be isolated intact from plasmid pPS29 on an ~2.3 kb HindIII restriction fragment. The construction of plasmid pPS29 is described in Example 5; a restriction site and function map of plasmid pPS29 is presented in FIG. 10 of the accompanying drawings.

The ~2.3 kb HindIII restriction fragment of plasmid pPS29 is isolated and inserted into partially HindIII-digested plasmid pPS44 to yield a variety of plasmids that comprise not only the activating sequence of the *Cephalosporium acremonium* isopenicillin N synthetase gene positioned to drive expression of the *Penicillium chrysogenum* isopenicillin N synthetase gene but also the hygromycin resistance-conferring gene from plasmid pPS29.

Figure 11:
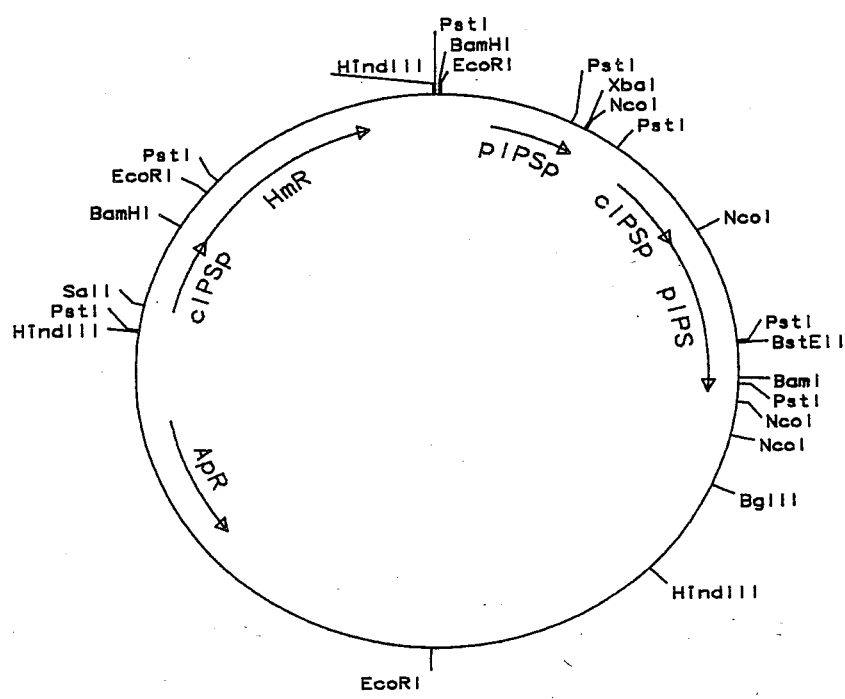
FIG. 11. A restriction site and function map of plasmid pPS45A.1.
Figure 12:
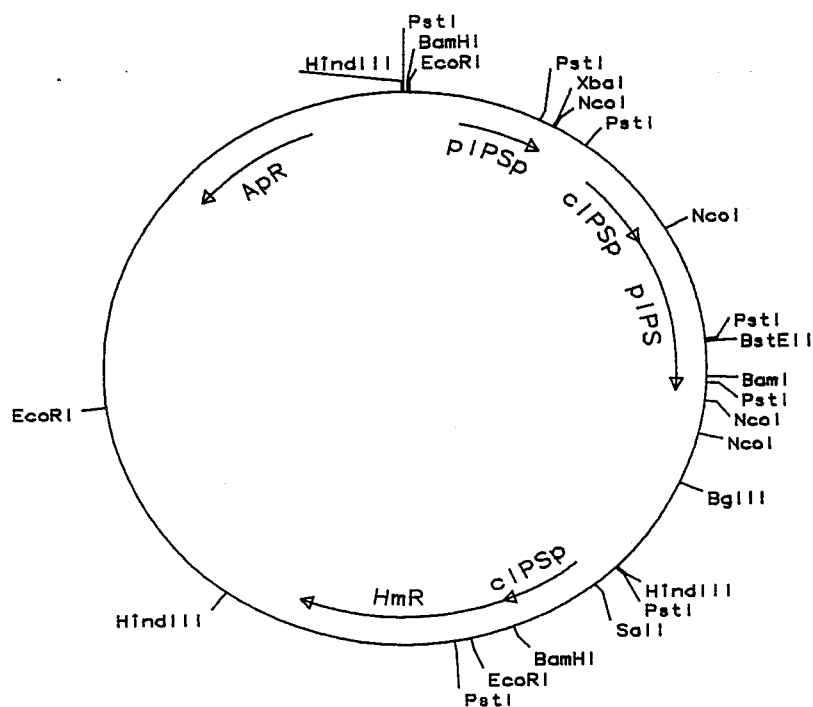
FIG. 12. A restriction site and function map of plasmid pPS45B.1.

Because plasmid pPS44 comprises two HindIII restriction sites, either of which is suitable for insertion of the hygromycin resistance-conferring fragment of plasmid pPS29, and because the HindIII restriction fragment of plasmid pPS29 can insert into either HindIII site of plasmid pPS44 in either of two orientations, four plasmids result from the insertion. These four plasmids, designated pPS45A.1, pPS45A.2, pPS45B.1, and pPS45B.2, drive expression of isopenicillin N synthetase activity in, and confer hygromycin resistance to, both *Penicillium chrysogenum* and *Cephalosporium acremonium*. Restriction site and function maps of plasmids pPS45A.1 and pPS45B.1 are respectively provided in FIGS. 11 and 12 of the accompanying drawings. Plasmids pPS45A.2 and pPS45B.2 differ from their pPS45A.1 and pPS45B.1 counterparts only with respect to orientation of the inserted ~2.3 kb HindIII restriction fragment of plasmid pPS29. The construction of plasmids pPS45A.1, pPS45A.2, pPS45B.1, and pPS45B.2 is described in Example 6.

Figure 13:
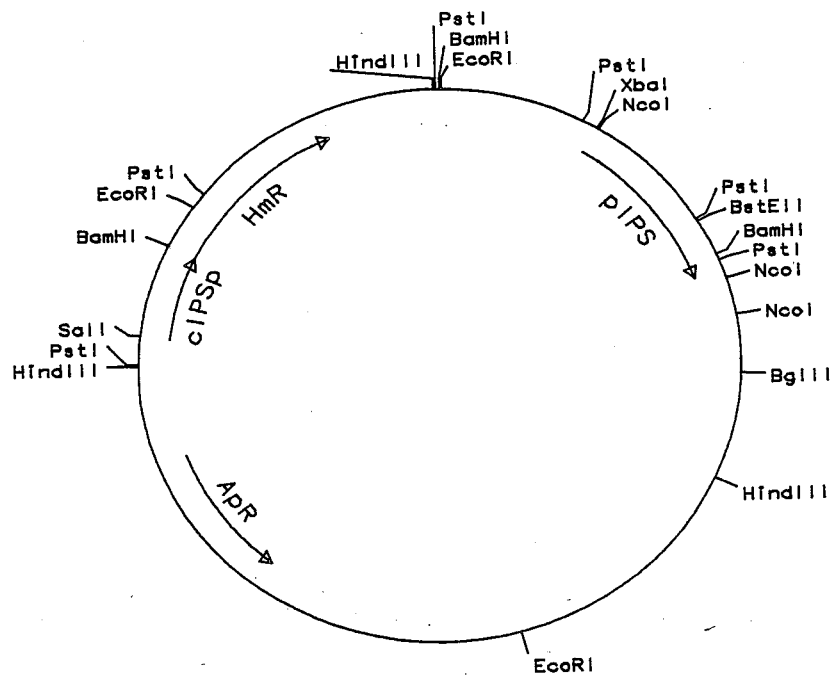
FIG. 13. A restriction site and function map of plasmid pPS42A.1.
Figure 14:
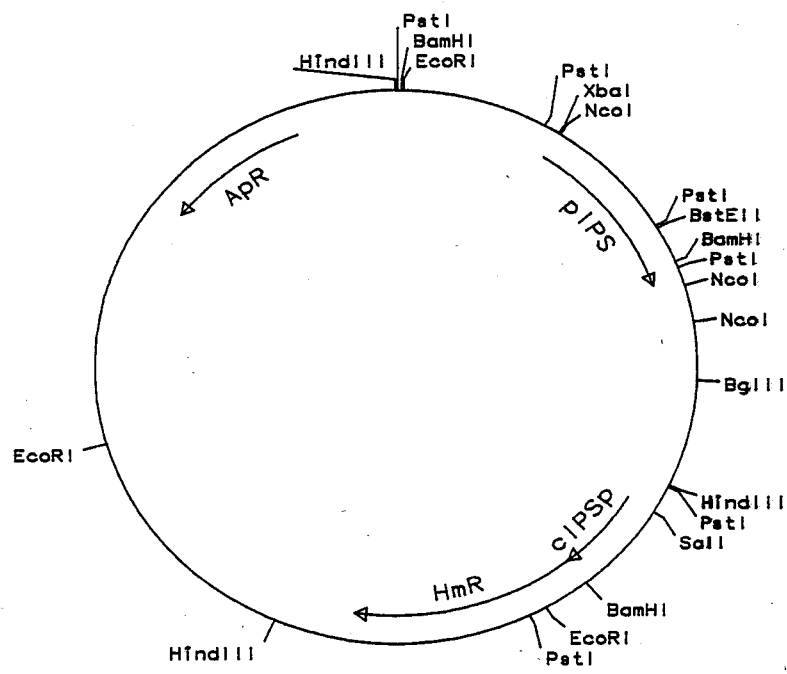
FIG. 14. A restriction site and function map of plasmid pPS42B.1.

Plasmid pLC2 can also be modified to comprise the hygromycin resistance-conferring gene of plasmid pPS29. Plasmid pLC2 comprises two HindIII restriction sites, either of which is suitable for the insertion of the ~2.3 kb HindIII restriction fragment of plasmid pPS29. Consequently, insertion of the ~2.3 kb HindIII restriction fragment of plasmid pPS29 into singly-cut, HindIII-digested plasmid pLC2 yields four plasmids, designated pPS42A.1, pPS42A.2, pPS42B.1, and pPS42B.2. Restriction site and function maps of plasmids pPS42A.1 and pPS42B.1 are respectively presented in FIGS. 13 and 14 of the accompanying drawings. The construction of plasmids pPS42A.1, pPS42A.2, pPS42B.1, and pPS42B.2 is described in Example 7.

Because plasmid pLC2 comprises almost 0.9 kb of the genomic DNA that was located upstream of the isopenicillin N synthetase-encoding DNA in the *Penicillium chrysogenum* genome, plasmid pLC2 necessarily comprises the transcription and translation activating sequence of the isopenicillin N synthetase-encoding DNA. Most transcription and translation activating sequences are encoded upstream of the DNA to be activated, although some ribosomal RNA-encoding DNA sequences are activated by transcription activating sequences that are not located upstream of the coding region. "Upstream" is a word used in the art of molecular biology and, in the present context, refers to DNA in the 5' direction from the 5' end of the coding strand of the isopenicillin N synthetase-encoding DNA.

The *Penicillium chrysogenum* transcription and translation activating sequence encoded on plasmid pLC2 is correctly positioned to drive expression of the isopenicillin N synthetase activity-encoding DNA, because in the construction of plasmid pLC2 no deletions or insertions affecting the transcription and translation activating sequence were introduced in the DNA flanking the 5' end of the coding strand of the isopenicillin N synthetase activity-encoding DNA. Because the *Penicillium chrysogenum* transcription and translation activating sequence located on plasmid pLC2 can be used to drive expression of a wide variety of DNA sequences, the activating sequence comprises an important part of the present invention. The activating sequence of the *P. chrysogenum* isopenicillin N synthetase gene is known to be encoded on the ~820 bp EcoRI-NcoI restriction fragment located immediately upstream of and adjacent to the isopenicillin N synthetase activity-encoding DNA on plasmid pLC2. Any restriction fragment that comprises the aforementioned ~820 bp EcoRI-NcoI restriction fragment necessarily comprises the *P. chrysogenum* transcription and translation activating sequence of the present invention.

There is sequence data on the *Penicillium chrysogenum* transcription and translation activating sequence encoded on plasmid pLC2. The sequence below is the DNA sequence that is upstream of the isopenicillin N synthetase activity-encoding DNA present on plasmid pLC2. Only a portion of the sequence of the ~820 bp EcoRI-NcoI restriction fragment that comprises the activating sequence is known, as is illustrated by the "XXXXXXXXXX" region depicted in the sequence. In order to further clarify how the activating sequence is oriented in plasmid pLC2, the restriction fragment is illustrated with single-stranded DNA overlaps characteristic of restriction enzyme EcoRI and NcoI cleavage.

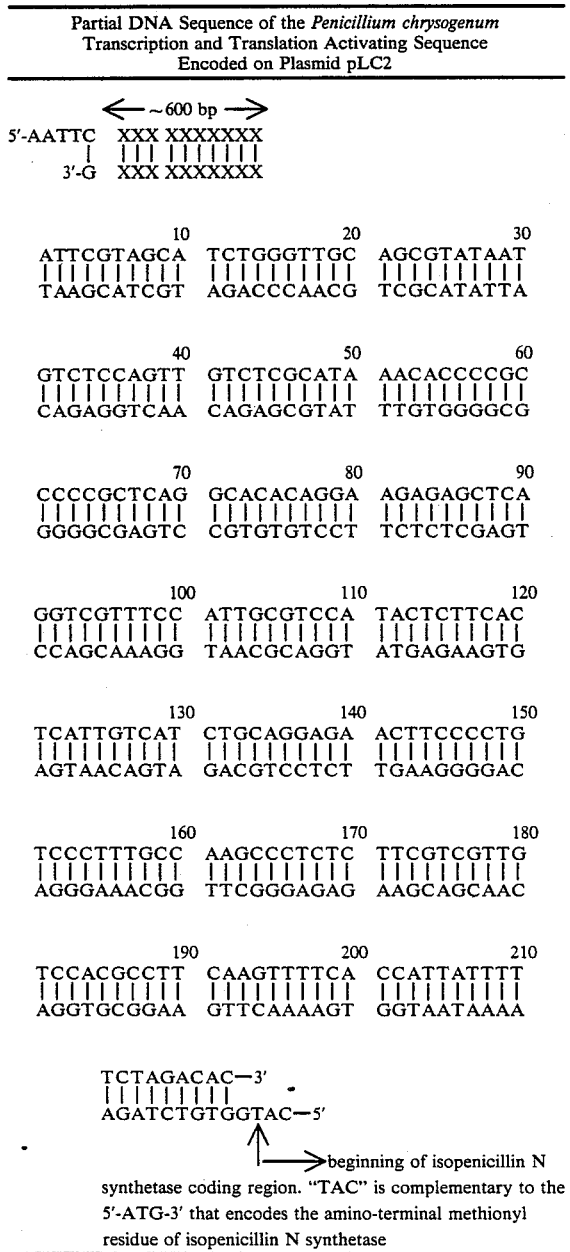

The *Penicillium chrysogenum* transcription and translation activating sequence can be used to drive expression of any DNA sequence, as plasmid pPS39 illustrates. Plasmid pPS39 is a derivative of plasmid pPS28, described in Example 5, that results from the replacement of the *Cephalosporium acremonium* transcription and translation activating sequence used to drive expression of the hygromycin resistance-conferring gene with the *P. chrysogenum* transcription and translation activating sequence of the present invention.

A useful intermediate plasmid, designated plasmid pPS38, is used in the construction of plasmid pPS39. Plasmid pPS38 is constructed by isolating the ~0.83 kb BamHI-NcoI restriction fragment of plasmid pLC2 that comprises the activating sequence of the isopenicillin N synthetase gene, attaching linkers with BamHI and NcoI-compatible, single-stranded overlaps to the ~0.83 kb BamHI-NcoI fragment, digesting the resulting fragment with BamHI, and ligating the resulting plasmid pLC2-derived, ~0.84 kb BamHI restriction fragment to BamHI-digested plasmid pUC8. This ligation produces two plasmids, designated pPS38 and pPS38.1, that differ only with respect to the orientation of the inserted BamHI restriction fragment. Plasmid pUC8 is available from Pharmacia P-L Biochemicals. 800 Centennial Ave., Piscataway, N.J. 08854.

Plasmid pPS38 is digested with restriction enzyme BamHI, and the ~0.84 kb BamHI restriction fragment that comprises the transcription and translation activating sequence is isolated and ligated with BamHI-digested plasmid pPS28. This ligation produces two plasmids, designated pPS39 and pPS39.1. Plasmid pPS39 results from the ligation of the ~0.84 kb BamHI restriction fragment of plasmid pPS38 with the ~5.8 kb BamHI restriction fragment of plasmid pPS28 and comprises the transcription and translation activating sequence of the isopenicillin N synthetase gene located in the proper orientation to drive expression of the hygromycin resistance-conferring gene. The linkers used in the construction of plasmid pPS38 ensure that the proper reading frame is maintained in plasmid pPS39 for expression of the hygromycin resistance-conferring gene.

Figure 15:
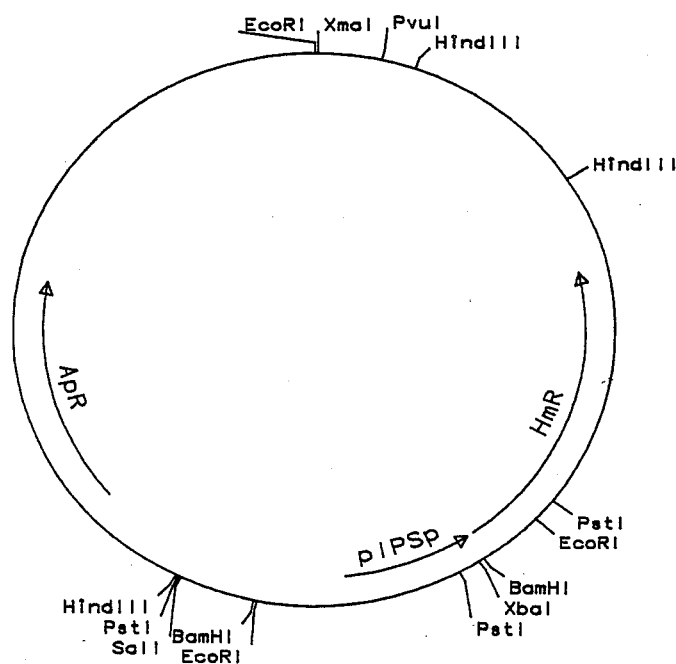
FIG. 15. A restriction site and function map of plasmid pPS39.

Plasmid pPS39.1 is analogous to plasmid pPS39, except the activating sequence is positioned in the opposite orientation and therefore does not drive expression of the hygromycin resistance-conferring gene. Plasmid pPS39.1 is thus useful as a negative control in transformation experiments and as a cloning vector. The construction of plasmids pPS39 and pPS39.1 is described in Example 8; a restriction site and function map of plasmid pPS39 is presented in FIG. 15 of the accompanying drawings.

The *Penicillium chrysogenum* transcription and translation activating sequence can be used to express any DNA sequence in *P. chrysogenum*, as indicated by the expression vectors described above. Thus, the present invention comprises the use of the *P. chrysogenum* transcription and translation activating sequence encoded within the ~0.82 kb EcoRl-NcoI restriction fragment of plasmid pLC2 to drive expression of any DNA sequence that encodes a useful substance. The *P. chrysogenum* activating sequence can also be used to drive expression of gene products in *Cephalosporium acremonium*.

The present invention results from the cloning of an intact, functional, *Penicillium chrysogenum* DNA sequence that encodes not only the amino acid sequence of isopenicillin N synthetase but also the transcription and translation activating sequence necessary to drive expression of isopenicillin N synthetase in *P. chrysogenum*. Likewise, the isopenicillin N synthetase gene of the present invention comprises the sequences located downstream of the coding region that are responsible for terminating transcription and for providing the mRNA polyadenylation and processing signals. Usually, the sequences responsible for transcription termination, mRNA polyadenylation, and mRNA processing are encoded within the region ~500 bp downstream of the stop codon of the coding region. Therefore, the ~0.65 kb BamHI-BqlII restriction fragment that comprises the isopenicillin N synthetase carboxy-terminal-encoding DNA and downstream sequences thereof also comprises the transcription termination and mRNA polyadenylation and processing signals of the isopenicillin N synthetase gene.

Figure 16:
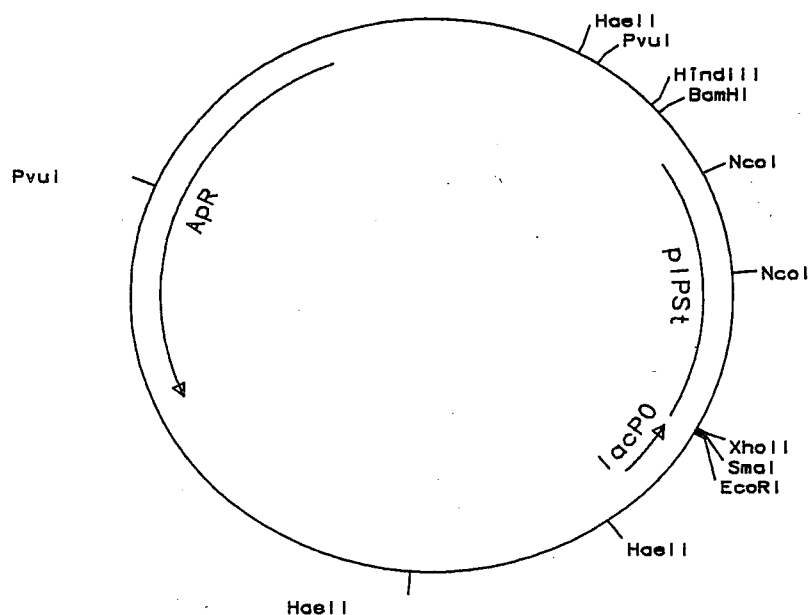
FIG. 16. A restriction site and function map of plasmid pPS41.

A vector of the present invention, designated plasmid pPS40, contains the transcription and translation activating sequence of the *Penicillium chrysogenum* isopenicillin N synthetase gene, followed by the hygromycin resistance-conferring gene, followed by the transcription termination and mRNA polyadenylation and processing signals of the *Penicillium chrysogenum* isopenicillin N synthetase gene. To construct plasmid pPS40, the ~0.65 kb BamHI-BglII restriction fragment of plasmid pLC2 is inserted into BamHI-digested plasmid pUC8 to yield plasmid pPS41 (FIG. 16).

Figure 17:
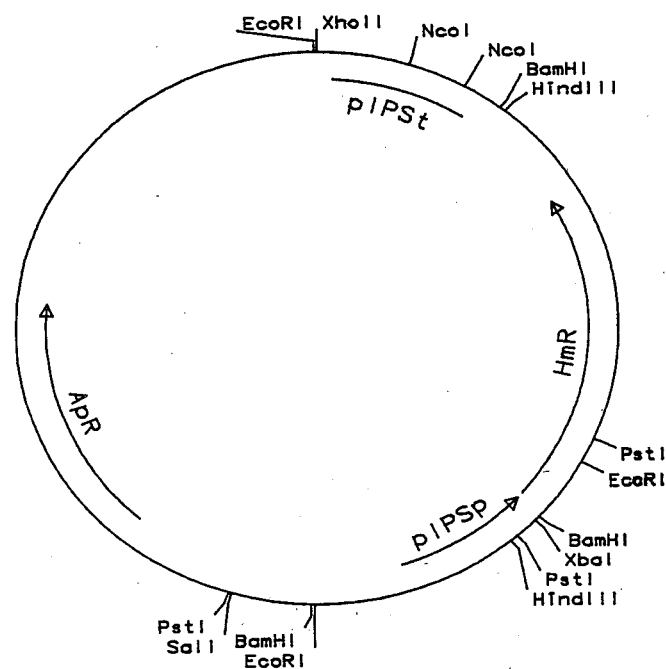
FIG. 17. A restriction site and function map of plasmid pPS40.

Plasmid pPS41 is digested with restriction enzymes EcoRI and HindIII, and the ~0.68 kb EcoRI-HindIII that comprises the transcription termination and mRNA polyadenylation and processing signals of the isopenicillin N synthetase gene is isolated. Plasmid pPS39 is then digested with restriction enzymes HindIII and EcoRI, and the HindIII-EcoRI digested plasmid pPS39 DNA is ligated to the ~0.68 kb HindIII-EcoRI restriction fragment of plasmid pPS41 to yield plasmid pPS40. The construction of plasmid pPS40 is described in Example 9, and a restriction site and function map of plasmid pPS40 is presented in FIG. 17 of the accompanying drawings.

The present invention results from the cloning of the isopenicillin N synthetase gene of *Penicillium chrysogenum* and comprises a number of useful vectors that utilize elements of that gene: the transcription and translation activating sequence; the coding region; and the transcription termination and mRNA polyadenylation and processing signals. Each of these elements is useful and can be used to construct expression vectors of great utility.

The activating sequence can be positioned on a recombinant DNA vector to drive expression of any DNA sequence that encodes a useful substance, such as isopenicillin N synthetase or a hygromycin resistance-conferring enzyme. Although not specifically exemplified herein, the activating sequence of the present invention can be used to drive expression of the isopenicillin N synthetase gene of *Cephalosporium acremonium*, which has been isolated as described in Ingolia et al., U.S. patent application Ser. No. 725,870, filed Apr. 22, 1985, Attorney Docket No. X-6722. The activating sequence of the present invention is not only useful in *Penicillium chrysogenum*, from which the sequence originates, but is also useful in other species in which it functions, such as *C. acremonium*.

Ultimate expression of a given DNA sequence on a recombinant DNA expression vector can be enhanced by placing a transcription termination and mRNA polyadenylation and processing signal at the 3' end of the coding strand of the coding region to be expressed. The present invention provides a transcription termination and mRNA polyadenylation and processing signal that can be used for the purposes of increasing expression from a recombinant DNA vector.

The present invention provides the coding sequence for the isopenicillin N synthetase gene of *Penicillium chrysogenum* and provides a number of expression vectors that drive expression of that gene in host cells such as *E. coli*, *P. chrysogenum*, and *Cephalosporium acremonium*. Production of isopenicillin N synthetase in *E. coli* allows for high-level expression and easy isolation of the enzyme so that the enzyme can be used to catalyze the condensation of novel tripeptides into novel antibiotic core structures in vitro. Transformation of *C. acremonium* and *P. chrysogenum* with the expression vectors of the present invention that drive expression of isopenicillin N synthetase in *C. acremonium* and *P. chrysogenum* leads to higher levels of isopenicillin N synthetase and thus leads to higher levels of antibiotic in the transformed cell.

The following Examples are provided to further illustrate and exemplify the present invention but are in no way intended to limit the scope of the present invention.

EXAMPLE 1

Culture of *E. coli* K12 JM109/pLC2 and Isolation of Plasmid pLC2

A. Culture of *E. coli* K12 JM109/pLC2

A lyophil of *E. coli* K12 JM109/pLC2 is obtained from the American Type Culture Collection, Rockville, Md., under the accession number ATCC 53334. The lyophil can be directly used as the "culture" in the process described below.

One liter of L-broth (10 g tryptone, 10 g NaCl, and 5 g yeast extract per liter) containing 50 µg/ml ampicillin was inoculated with a culture of *E. coli* K12 JM109/pLC2 and incubated in an air-shaker at 37° C. until the optical density at 590 nm (O.D.$_{590}$) was ~1 absorbance unit, at which time 150 mg of chloramphenicol were added to the culture. The incubation was continued for about 16 hours; the chloramphenicol addition inhibits protein synthesis, and thus inhibits further cell division, but allows plasmid replication to continue.

B. Isolation of Plasmid pLC2

The culture prepared in Example 1A was centrifuged in Sorvall GSA rotor (DuPont Co., Instrument Products, Biomedical Division, Newtown, Conn. 06470) at 6000 rpm for 5 minutes at 4° C. The resulting supernatant was discarded, and the cell pellet was washed in 40 ml of TES buffer (10 mM Tris-HCl, pH=7.5; 10 mM NaCl; and 1 mM EDTA) and then repelleted. After discarding the supernatant again, the cell pellet was frozen in a dry ice-ethanol bath and then thawed. The thawed cell pellet was resuspended in 10 ml of a solution of 25% sucrose and 50 mM EDTA. After adding and mixing 1 ml of a 5 mg/ml lysozyme solution; 3 ml of 0.25 M EDTA, pH=8.0; and 100 µl of 10 mg/ml RNAse A, the solution was incubated on ice for 15 minutes. Three ml of lysing solution (prepared by mixing 3 ml 10% Triton-X 100; 75 ml 0.25 M EDTA, pH=8.0; 15 ml of 1 M Tris-HCl, pH=8.0; and 7 ml of water) were added to the lysozyme-treated cells, mixed, and the resulting solution incubated on ice for another 15 minutes The lysed cells were frozen in a dry ice-ethanol bath and then thawed The cellular debris was removed from the solution by centrifugation at 25,000 rpm for 40 minutes in an SW27 rotor (Beckman, 7360 N. Lincoln Ave., Lincolnwood, Ill. 60646) and by extraction with buffered phenol. After adding 30.44 g of CsCl and ~1 ml of a 5 mg/ml ethidium bromide solution, the solution volume was adjusted to 40 ml and decanted into a VTi50 ultracentrifuge tube (Beckman). After sealing the tube, the solution was centrifuged in a VTi50 rotor at 42,000 rpm for ~16 hours. The resulting plasmid band, visualized with ultraviolet light, was isolated and then placed in a Ti75 tube and rotor (Beckman) and centrifuged at 50,000 rpm for 16 hours. Any necessary volume adjustments were made using TES containing 0.761 g/ml CsCl. The plasmid band was again isolated, extracted with salt-saturated isopropanol to remove the ethidium bromide, and diluted 1:3 with TES buffer. Two volumes of ethanol were then added to the solution, followed by incubation overnight at −20° C. The plasmid DNA was pelleted by centrifuging the solution in an SS34 rotor (Sorvall) for 15 minutes at 10,000 rpm.

The ~1 mg of plasmid pLC2 DNA obtained by this procedure was suspended in 1 ml of TE buffer (10 mM Tris-HCl, pH=8.0 and 1 mM EDTA) and stored at −20° C. A restriction site and function map of plasmid pLC2 is presented in FIG. 2 of the accompanying drawings.

EXAMPLE 2

Construction of Plasmid pLC3

A. Culture of *E. coli* K12 RV308/pCZ106 and Isolation of Plasmid pCZ106.

A lyophil of a culture of *E. coli* K12 RV308/pCZ106 is obtained from the Northern Regional Research Laboratories, Peoria, Ill., under the accession number NRRL B-15959. The lyophil is used to inoculate 1 liter of L-broth containing 50 μg/ml kanamycin, and the inoculated broth is incubated at 25° C. in an air-shaker until the 0.D.590 is between 0.5 and 1.0 absorbance units. When the culture reaches 0.5–1.0 absorbance units in optical density, the temperature is raised to 37° C. and incubation is continued for 2 to 6 hours. The runaway replicon, as stated previously herein, is temperature sensitive and loses copy number control at 37° C. The 2 to 6 hour incubation at 37° C. provides ample time for uncontrolled replication.

After the 2 to 6 hour incubation at 37° C., the cells are collected, and the plasmid pCZ106 DNA is isolated in substantial accordance with the procedure of Example 1B. About 5 mg of plasmid pCZ106 DNA is obtained and suspended in 5 ml of TE buffer. A restriction site and function map of plasmid pCZ106 is provided in FIG. 3 of the accompanying drawings.

B. NcoI and BamHI Digestion of Plasmid pCZ106 and Isolation of the ~8.7 kb NcoI-NcoI and ~1.6 kb NcoI-BamHI Restriction Fragments of Plasmid pCZ106

Approximately 25 μg, corresponding to 25 ~1, of the plasmid pCZ106 DNA prepared in Example 2A. were added to and mixed with 10 ¾l of 10X BamHI reaction buffer (1.5 M NaCl; 60 mM Tris-HCl, pH=7.9; 60 mM MgCl₂; and 1 mg/ml bovine serum albumin (BSA)), 5 ~1 (~50 units) restriction enzyme* BamHI, 5 ¾l (~50 units) restriction enzyme NcoI, and 55 ¾l of H₂O. The resulting reaction was incubated at 37° C. for four hours, after which time the reaction was essentially complete.

The NcoI-BamHI reaction mixture was then electrophoresed on a 1% agarose gel until the desired ~1.6 kb NcoI-BamHI and ~8.7 kb NcoI-NcoI fragments were clearly separated from the other digestion product, an ~0.3 kb restriction fragment. Visualization of the electrophoresed DNA was accomplished by staining the gel in a dilute solution (0.5 μg/ml) of ethidium bromide and exposing the stained gel to long-wave UV light. After locating the desired fragments, a small slit was made in the gel in front of each of the desired fragments, and a small piece of Schleicher and Schuell (Keene, N.H. 03431) NA-45 DEAE membrane was placed in each slit. Upon further electrophoresis, the DNA non-covalently bound to the DEAE membrane. After the desired fragments were bound to the DEAE membrane, the membranes were removed and rinsed with low salt buffer (100 mM NaCl; 0.1 mM EDTA; and 20 mM Tris-HCl, pH=8). Next, each membrane was placed in a small tube and immersed in high salt buffer (1 M NaCl; 0.1 mM EDTA; and 20 mM Tris-HCl, pH=8) and then incubated at 65° C. for one hour to remove the DNA from the DEAE paper. After the 65° C. incubation, the incubation buffer was collected and the membrane rinsed with high salt buffer. The rinse solution was pooled with the incubation buffer before collecting the desired DNA fragments.

The volume of the high salt-DNA solution was adjusted so that the NaCl concentration was 0.25 M, and then two volumes of cold, absolute ethanol were added. The resulting solutions were mixed and placed at −70° C. for 10–20 minutes. After chilling, the solutions were centrifuged at 15,000 rpm for 15 minutes. After another precipitation to remove residual salt, the DNA pellets were rinsed with ethanol, dried, resuspended in 20 μl of TE buffer, and constituted ~5.0 μg each of the desired ~1.6 kb NcoI-BamHI and ~8.7 kb NcoI-NcoI restriction fragments of plasmid pCZ106. The purified fragments obtained were individually dissolved in 25 μl of TE buffer and stored at −20° C.

*Unless otherwise noted, restriction and ligation enzymes were obtained from New England Biolabs, 32 Tozer Road, Beverly, Mass. 01915. Unit definitions herein correspond to the particular manufacturer's unit definitions.

C. NcoI and BglII Digestion of Plasmid pLC2 and Isolation of the ~1.6 kb NcoI-BglII Restriction Fragment that Encodes Isopenicillin N Synthetase Approximately 25 μg, corresponding to 25 ¾l of the plasmid pLC2 DNA prepared in Example 1B were dissolved in 10 μl 10X BamHI buffer and 60 μl of H₂O. About 5 μl (50 units) of restriction enzyme BglII were added to the solution of plasmid pLC2 DNA, and the resulting reaction was incubated at 37° C. for two hours. Then, about 5 ¾l (50 units) of restriction enzyme NcoI were added to the reaction mixture and the resulting reaction was incubated at 37° C. for 5 minutes. After 5 minutes reaction, the NcoI digestion was stopped by incubating the reaction mixture at 70° C. for 10 minutes. A partial NcoI digestion was obtained. The NcoI-BglII-digested DNA obtained was loaded onto a 1% agarose gel and the desired ~1.6 kb NcoI-BglII restriction fragment was isolated in substantial accordance with the procedure of Example 2B. Approximately 5 μg of the desired fragment were obtained, suspended in 25 μl of TE buffer, and stored at −20° C.

D. Final Construction of Plasmid pLC3

Five μl of the ~1.6 kb NcoI-BamHI and 2.5 μl of the ~8.7 kb NcoI-NcoI restriction fragments of plasmid pCZ106 purified in Example 2B are ligated to five μl of the ~1.6 kb NcoI-BglII restriction fragment of plasmid pLC2 purified in Example 2C to form plasmid pLC3. The reaction volume is 30 μl and comprises the aforementioned DNA fragments, 1.1 μl (~100 units) T4 DNA 15 ligase, 3 μl 10X ligation buffer (0.5 M Tris-HCl, pH=7.8; 100 mM MgCl2; 200 mM dithiothreitol (DTT); 10 mM ATP; and 1 mg/ml BSA), and 13.4 μl of H₂O. The reaction is incubated at 15° C. for 2 hours, after which time the reaction is essentially complete. The ligated DNA constitutes the desired plasmid pLC3 DNA. A restriction site and function map of plasmid pLC3 is presented in FIG. 4 of the accompanying drawings.

EXAMPLE 3

Construction of *E. coli* K12 RV308/pLC3 and Assay of *E. coli*-Produced Isopenicillin N Synthetase A. Construction of *E. coli* K12 RV308/pLC3

A 50 ml culture of *E. coli* K12 RV308 (NRRL B-15624) in L-broth was grown to an O.D.$_{590}$ of ~0.5 absorbance units. The culture was chilled on ice for ten minutes, and the cells were collected by centrifugation. The cell pellet was resuspended in 25 ml of cold 100 mM CaCl₂ and incubated on ice for 25 minutes. The cells were once again pelleted by centrifugation, and the pellet was resuspended in 2.5 ml of cold 100 mM CaCl₂ and incubated on ice overnight.

Two hundred μl of this cell suspension are mixed with the ligated DNA prepared in Example 2D and incubated on ice for 20 minutes, and then the cells are collected by centrifugation. The cell pellet is resuspended in ~1 ml of L-broth, and the suspension is incubated at 25° C. for one hour. Aliquots of the cell mixture are plated on L-agar (L-broth with 15 g/l agar) plates containing 50 μg/ml kanamycin, and the plates are incubated at 25° C. *E. coli* K12 RV308/pLC3 transformants are verified by selection for kanamycin resistance and by restriction enzyme analysis of the plasmid DNA of the transformants. Plasmid DNA is obtained from the *E. coli* K12 RV308/pLC3 transformants in substantial accordance with the teaching of Example 2A, but on a smaller scale, and the CsCl-gradient steps are omitted.

B. Culture of *E. coli* K12 RV308/pLC3 for Expression of Isopenicillin N Synthetase Activity Several isolates of the *E. coli* K12 RV308/pLC3 transformants prepared in Example 3A are individually inoculated into 5 ml aliquots of L-broth containing 50 μg/ml kanamycin, and the cultures are incubated in an air-shaker at 25° C. until the OD590 is ~0.2 absorbance units. The cultures are then transferred to a 37° C. air-shaker and incubated at 37° C. for ~6 hours.

After the six-hour, 37° C. incubation, one ml of each culture is collected, and the cells are pelleted by centrifugation. The cell pellets are individually washed with 1 ml of 10 mM NaCl and then resuspended in 1.0 ml of IPS extraction buffer (0.05 M Tris-HCl, pH=8.0; 0.01 M KCl; and 0.01 M MgSO₄). The cells are sonicated by six, five-second bursts of sonication delivered by a Sonifier Cell Disruptor, Model W185, Heat Systems-Ultrasonics, Inc., Plainview, Long Island, N.Y., using the micro tip. The time between bursts of sonication is 60 seconds, and the mixture is kept in an ice-ethanol bath during the procedure. After sonication, the cell mixture is centrifuged to remove debris and then used directly in the assay.

C. Assay for Isopenicillin N Synthetase Activity

The following assay procedure is derived from the procedure of Shen et al., 1984, J. of Antibiotics 37(9): 1044-1048.

The isopenicillin N synthetase assay reaction is carried out in a total volume of 500 μl. To start o the reaction, 1.0 ml of a solution of 1.4 mM δ-(L-α-aminoadipyl)-L-cysteinyl-D-valine and 3.75 mM DTT is allowed to react at room temperature for 30-60 minutes to reduce any dimeric tripeptide to the monomeric form. Fifty μl of each of the following stock solutions are aliquoted into each assay tube (sterile, glass, disposable 13×100 mm tubes): 500 mM Tris-HCl, pH=7.4; 100 mM KCl; 100 mM MgSO₄; 2.0 mM FeSO₄; and 6.7 mM ascorbic acid. Next, varying amounts of extract, diluted with water to a volume of 150 μl, are added. About 100 μl aliquots of the tripeptide solution are then added to each tube; the addition of the tripeptide starts the reaction. Each tube is vortexed upon addition of the substrate. The reaction mixture vessels are then placed in a gyrotory shaker bath at 250 rpm, with an incubation temperature of 25° C. The reaction time is 45 minutes.

After 45 minutes of reaction, 2 samples of 100 μl each are withdrawn and dispensed into wells in the bioassay plates, and 100 units of penicillinase A are added to the remainder of the sample. The penicillinase A is obtained from Riker's Laboratories, Inc.; the enzyme is sold in vials of 100,000 units, which are rehydrated to 5.0 mls with H₂O. Five μl (100 units) of the rehydrated penicillinase A are added to the remainder of each reaction mixture, allowed to react for 5 minutes at room temperature, and then 100 μl of each penicillinase A-treated extract is dispensed into the wells of a bioassay plate. This penicillinase A treatment is done to check that the zones on the bioassay plate are due to the presence of a penicillin rather than a cephalosporin or other contaminant.

The penicillin N standard curve is prepared by adding 0.5, 1.0, 2.0, 5.0, 10.0, and 20.0 μg of penicillin N to bioassay wells. The penicillinase A activity is also checked by adding 5 μl of the enzyme preparation to ~200 μl of 0.2 μg/ml penicillin N.

The bioassay plates are composed of K131 nutrient agar, which is prepared by dissolving 30.5 g BBL Antibiotic Medium #11 (Becton Dickinson & Company, Cockeysville, Md.) in 1 liter of deionized water, bringing the solution to a boil, cooling to 70° C., and then autoclaving 35 minutes at 121° C. and 15 psi. The plates are seeded with 4 mls of fresh overnight culture of *Micrococcus luteus* (ATCC 9341) per 700 ml of agar. The *M. luteus* is grown in K544 nutrient broth, which is composed of: Difco peptone, 5.0 g; Difco yeast extract, 1.5 g; sodium chloride, 3.5 g; dipotassium phosphate (anhydrous), 3.7 g; monopotassium phosphate, 1.3 g; Difco beef extract, 1.5 g, in 1 liter of deionized water—the solution is brought to a boil, cooled to 25° C., adjusted to a pH=7.0 with 1 N HCl or 1 N NaOH, and then autoclaved for 20 minutes at 121° C. and 15 psi before use. The seeded agar is dispensed into 100×15 mm plates, at 15 mls of seeded agar per plate. The wells are prepared by applying suction using a disposable 5 ml pipette; each well is 10 mM in diameter.

After the plates are prepared and the samples are dispensed into the wells, the plates are placed in a 37° C. incubator for 18 hours. The assay results are determined by measuring the diameter of the cleared areas around each sample well, which result from the *M. luteus* being unable to grow when a penicillin is present.

The results of the assay demonstrate that the *E. coli* K12 RV308/pLC3 transformants express isopenicillin N synthetase activity.

EXAMPLE 4

Construction of Plasmid pPS44

A NcoI Digestion of Plasmid pIT335 DNA and Isolation of the Resulting ~0.85 kb Fragment that Encodes a *Cephalosporium acremonium* Transcription and Translation Activating Sequence Approximately 50 μl, corresponding to 50 μg, of plasmid pIT335 DNA, which can be prepared in substantial accordance with the procedure of Example 1, were added to and mixed with 10 μl 10X BamHI buffer, 5 μl (~50 units) restriction enzyme NcoI, and 35 μl of H$_2$O. The resulting reaction was incubated at 37° C. for four hours. The reaction mixture was then made 0.25 M in NaCl, diluted with two volumes of absolute ethanol, chilled for 10 minutes in a dry ice-ethanol bath, and centrifuged to pellet the precipitated DNA.

The NcoI-digested plasmid pIT335 DNA was then loaded onto a 1% agarose gel for electrophoresis. The ~0.85 kb restriction fragment that comprises the *Cephalosporium acremonium* transcriptional and translational activating sequence of the isopenicillin N synthetase gene was isolated from the gel and purified in substantial accordance with Example 2B. About 4 μg of the desired fragment were obtained and suspended in 10 μl of TE buffer.

B. Preparation of Partially NcoI-Digested Plasmid pLC2

About 25 μg of plasmid pLC2 DNA are dissolved in 10 μl of 10X BamHI buffer and 80 μl of H$_2$O. About 10 μl (100 units) of restriction enzyme NcoI are added to the solution of plasmid pLC2 DNA, and the resulting reaction is incubated at 37° C. for three minutes. The reaction is then stopped by extraction with buffered phenol. The short reaction time is designed to obtain partially NcoI-digested plasmid pLC2 DNA.

The reaction mixture is loaded onto a 1% agarose gel and electrophoresed until the band corresponding to linear plasmid pLC2 DNA is separated from uncut plasmid and other reaction products. The linear plasmid pLC2 DNA is then isolated in substantial accordance with the procedure of Example 2B; about 5 μg of linear plasmid pLC2 are obtained and suspended in 10 μl of TE buffer C. Final Construction of Plasmid pPS44

About 2 μl of the ~0.85 kb NcoI restriction fragment of plasmid pIT335 are mixed with about 4 μl of the partially NcoI-digested plasmid pLC2 DNA prepared in Example 4B. About 3 μl 10X ligase buffer, 19 μl of H$_2$O and 2 μl T4 DNA ligase are added to the mixture of DNA, and the resulting reaction is incubated at 16° C. for two hours. The ligated DNA constitutes the desired plasmid pPS44 DNA. A restriction site and function map of plasmid pPS44 is presented in FIG. 5 of the accompanying drawings. The ligated DNA is used to transform *E. coli* K12 JA221, as described below.

D. Construction of *E. coli* K12 JA221/pPS44 and Isolation of Plasmid pPS44 DNA

A 50 ml culture of *E. coli* K12 JA221 (NRRL B-15211) in L-broth was grown to an O.D.$_{590}$ of ~0.2. The culture was chilled on ice for ten minutes, and the cells were collected by centrifugation. The cell pellet was resuspended in 25 ml of cold 100 mM CaCl$_2$ and incubated on ice for 25 minutes. The cells were once again pelleted by centrifugation, and the pellet was resuspended in 2.5 ml of cold 100 mM CaCl$_2$ and incubated on ice overnight.

Two hundred μl of this cell suspension are mixed with the ligated DNA prepared in Example 4C and incubated on ice for 20 minutes. The mixture is then incubated at 40° C. for 2 minutes, followed by a 10 minute incubation at room temperature. Three ml of L-broth are added to the cell mixture, and then the cells are incubated in an air-shaker at 37° C. for two hours.

Plasmid pLC2 has three NcoI sites. Plasmid pPS44 can only be constructed by insertion of the ~0.85 kb NcoI restriction fragment of plasmid pIT335 into one particular NcoI site of plasmid pLC2, and the fragment must be inserted in the proper orientation. Plasmid pPS44 can be identified by PstI digestion and analysis of the digestion products, because the ~0.85 kb NcoI restriction fragment of plasmid pIT335 comprises an internal PstI restriction site. Digestion of plasmid pPS44 with PstI generates fragments of 5.3 kb, 1.3 kb, 0.76 kb, 0.29 kb, and 0.25 kb.

EXAMPLE 5

A. Construction of Intermediate Plasmid pPS19

Figure 6:
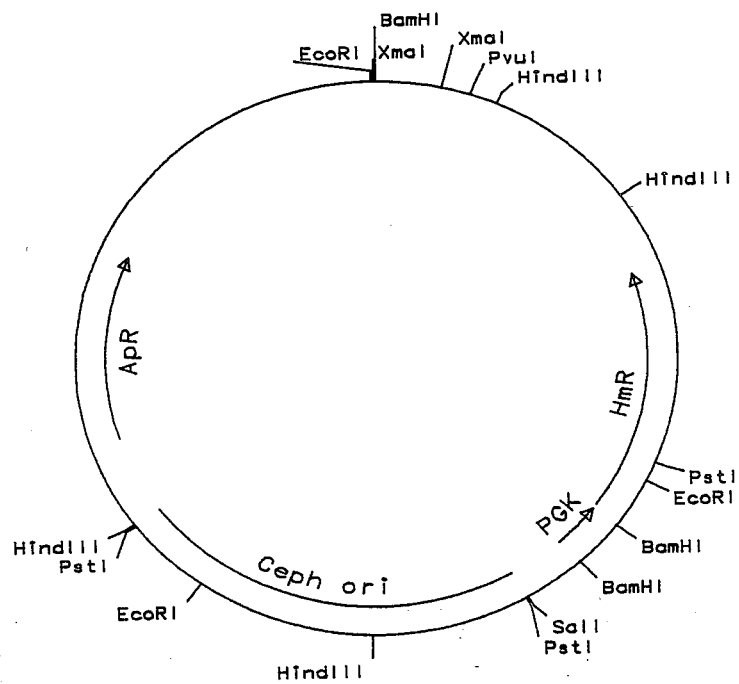
FIG. 6. A restriction site and function map of plasmid pIT221.

Chapman et al., U.S. patent application Ser. No. 654,919, filed Sept. 27, 1984, Attorney Docket No. X-6570, discloses vectors and conditions for transforming *Cephalosporium acremonium*. Construction flow sheets 1-6 and Examples 1-6 of U.S. patent application Ser. No. 654,919, incorporated herein by reference, disclose the construction of plasmid pIT221. A restriction site and function map of plasmid pIT221 is provided in FIG. 6 of the accompanying drawings.

One μg of plasmid pIT221 DNA was dissolved in five μl of 10X XmaI buffer (250 mM NaCl; 60 mM Tris-HCl, pH=7.5; 60 mM MgCl$_2$; 60 mM 2-mercaptoethanol; and 1 mg/ml BSA), 43 μl of H$_2$O, and 2 μl (~10 units) of restriction enzyme XmaI. The resulting reaction was incubated at 37° C. for four hours. The reaction was terminated by a phenol extraction. After further extracting the XmaI reaction mixture with CHCl$_3$, the reaction mixture was made 0.25 M in NaCl, diluted with 2 volumes of absolute ethanol, chilled for 10 minutes in a dry ice-ethanol bath, and the precipitated, XmaI-digested plasmid pIT221 DNA was pelleted by centrifugation.

Figure 7:
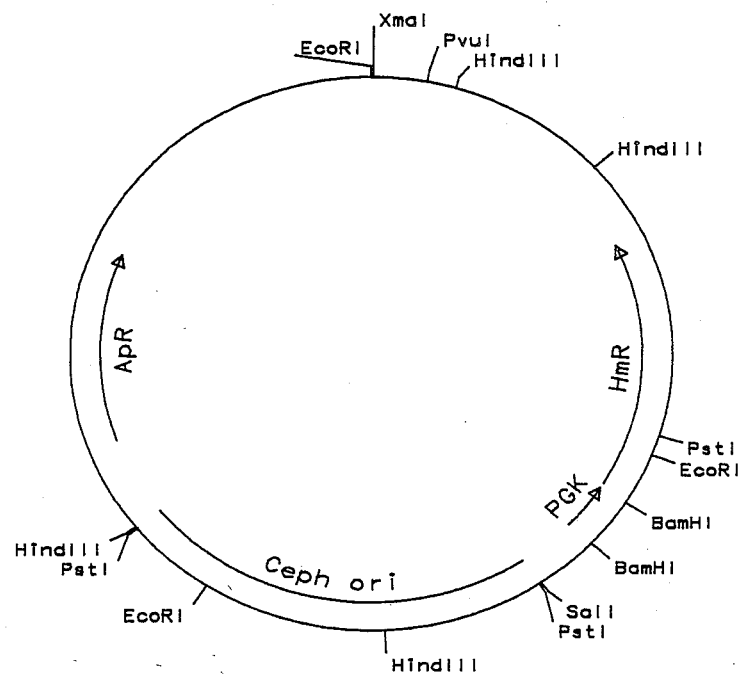
FIG. 7. A restriction site and function map of plasmid pPS19

The XmaI-digested plasmid pIT221 DNA was redissolved in 100 μl of 1X ligation buffer containing 500 units of T4 DNA ligase. The ligation reaction was incubated at 12° C. for ~16 hours and then used to transform *E. coli* K12 JA221 in substantial accordance with the procedure of Example 4D. The ampicillin-resistant, plasmid pPS19 transformants were identified by restriction enzyme analysis of the plasmid DNA of the transformants. Plasmid pPS19 differs from plasmid pIT221 in that plasmid pPS19 does not comprise the ~0.3 kb XmaI restriction fragment found in plasmid pIT221. Plasmid pPS19 DNA was prepared in substantial accordance with the procedure of Example 1. A restriction site and function map of plasmid pPS19 is presented in FIG. 7 of the accompanying drawing.

B. Construction of Intermediate Plasmids pPS23 and pPS23.1

(i) Preparation of BamHI-digested plasmid pUC8.

About 5 μg of plasmid pUC8 (obtained from Pharmacia P-L Biochemicals) were dissolved in 5 μl of 10X BamHI reaction buffer and 40 μl of H$_2$O. About 5 μl (50 units) of restriction enzyme BamHI were added to the solution of DNA, and the resulting reaction was incubated at 37° C. for two hours. The reaction was terminated by extraction with buffered phenol, followed by extraction with chloroform. The BamHI-digested plasmid pUC8 DNA was precipitated by adjusting the NaCl concentration to 0.25 M, adding 2 volumes of ethanol, and chilling at −70° C. for 10 minutes. The BamHI-digested plasmid pUC8 DNA was collected by centrifugation and resuspended in 5 μl of H$_2$O.

(ii) Isolation of the ~0.85 kb NcoI restriction fragment of plasmid pIT335.

About 10 μg of plasmid pIT335 were dissolved in 5 μl of 10X BamHI buffer and 40 μl of H₂O. About 5 μl (50 units) of restriction enzyme NcoI were added to the solution of DNA, and the resulting reaction was incubated at 37° C. for two hours. The reaction mixture was then loaded onto a 1% agarose gel, and the desired ~0.85 kb NcoI restriction fragment that comprises the transcription and translation activating sequence of the IPS gene was isolated in substantial accordance with the procedure of Example 2B. About 1 μg of the desired fragment was obtained and suspended in 5 μl of H₂O.

(iii) Preparation of the linker used in the construction of plasmid pPS23.

The single-strands of the following linker were synthesized using an automated DNA synthesizer:

About 75 picomoles of each single strand of the linker were individually dissolved in 22.5 μl of H₂O and 2.5 μl of ligase buffer. About 1 μl (10 units) of T4 DNA kinase (Bethesda Research Laboratories) was added to each solution of single-stranded DNA, and the reactions were incubated at 37° C. for 10 minutes. Following the kinase reaction, the reaction mixtures were incubated at 70° C. for 15 minutes. Then, to anneal the single-stranded DNA to form the linker, the two reaction mixtures were pooled, incubated at 65° C. for 10 minutes, incubated at room temperature for 2 hours, and then incubated at 4° C. overnight.

(iv) Final Construction of plasmids pPS23 and pPS23.1.

One μl of the BamHI-digested plasmid pUC8 DNA was added to a mixture of 4 μl of the ~0.85 kb NcoI restriction fragment of plasmid pIT335 and 10 μl of the annealed linker. About 4 μl of 10X ligase buffer, 2 μl (500 units) T4 DNA ligase, and 29 μl of H₂O were added to the mixture of DNA, and the resulting reaction was incubated at 4° C. overnight. The ligated DNA constituted the desired plasmids pPS23 and pPS23.1.

A 50 ml culture of E. coli K12 JM109, available from Pharmacia P-L Biochemicals, in L-broth was grown to an O.D.$_{590}$ of approximately 0.5 absorbance units. The culture was chilled on ice for ten minutes, and the cells were collected by centrifugation. The cell pellet was resuspended in 25 ml of cold 100 mM CaCl₂ and incubated on ice for 25 minutes. The cells were once again pelleted by centrifugation, and the pellet was resuspended in 2.5 ml of cold 100 mM CaCl₂ and incubated on ice overnight.

Two hundred μl of this cell suspension were mixed with the ligated DNA prepared above and incubated on ice for 20 minutes. At the end of this period, the cells were placed in a water bath at 42° C. for 2 minutes and then returned to the ice for an additional 10 minutes. The cells were collected by centrifugation and resuspended in one ml of L-broth and incubated at 37° C. for 2 hours.

Aliquots of the cell mixture were plated on L-agar (L-broth with 15 grams per liter agar) plates containing 100 μg ampicillin/ml, 40 μg X-gal/ml, and 40 μg IPTG/ml. The plates were incubated at 37° C. overnight. Colonies that contain a plasmid without an insert, such as E. coli K12 JM109/pUC8, appear blue on these plates. Colonies that contain a plasmid with an insert, such as E. coli K12 JM109/pPS23, are white. Several white colonies were selected and screened by restriction analysis of their plasmid DNA for the presence of the ~0.85 kb BamHI restriction fragment containing the IPS activating sequence. Plasmid DNA was obtained from the E. coli K12 JM109/pPS23 and E. coli K12 JM109/pPS23.1 cells in substantial accordance with the teaching of Example 2A.

About 50 μg of plasmid pPS23 DNA were dissolved in 15 μl of 10X BamHI reaction buffer and 125 μl of H₂O. About 10 μl (100 units) of restriction enzyme BamHI were added to the solution of DNA, and the resulting reaction was incubated at 37° C. for two hours. The BamHI-digested plasmid pPS23 DNA was loaded onto a 1% agarose gel, and the ~0.86 kb BamHI restriction fragment that comprises the activating sequence of the IPS gene was isolated in substantial accordance with the procedure of Example 2B. About 5 μg of the desired fragment were obtained and suspended in 10 μl of H₂O.

About 5 μg of plasmid pPS19 DNA were dissolved in 10 μl 10X BamHI reaction buffer and 85 μl of H₂O. About 5 μl (50 units) of restriction enzyme BamHI were added to the solution of plasmid pPS19 DNA, and the resulting reaction was incubated at 37° C. for two hours. The reaction mixture of BamHI-digested plasmid pPS19 DNA was extracted once with buffered phenol and then extracted twice with chloroform. The DNA was then precipitated, collected by centrifugation and resuspended in 10 μl of H₂O.

About 1 μl of the ~0.86 kb BamHI restriction fragment was added to 1 μl of the BamHI-digested plasmid pPS19 DNA, 3 μl 10X ligase buffer, 2 μl T4 DNA ligase, and 23 μl of H₂O. The resulting ligation reaction was incubated at 15° C. overnight. The ligated DNA constituted the desired plasmid pPS21A.

The ligated DNA was used to transform E. coli K12 C600, a strain available from the American Type Culture Collection, Rockville, Md. 20852, under the accession number ATCC 33525, in substantial accordance with the procedure of Example 5B(iv). The transformed cells were plated on L-agar plates containing 100 μg/ml ampicillin, and the plates were incubated at 37° C. overnight.

Figure 8:
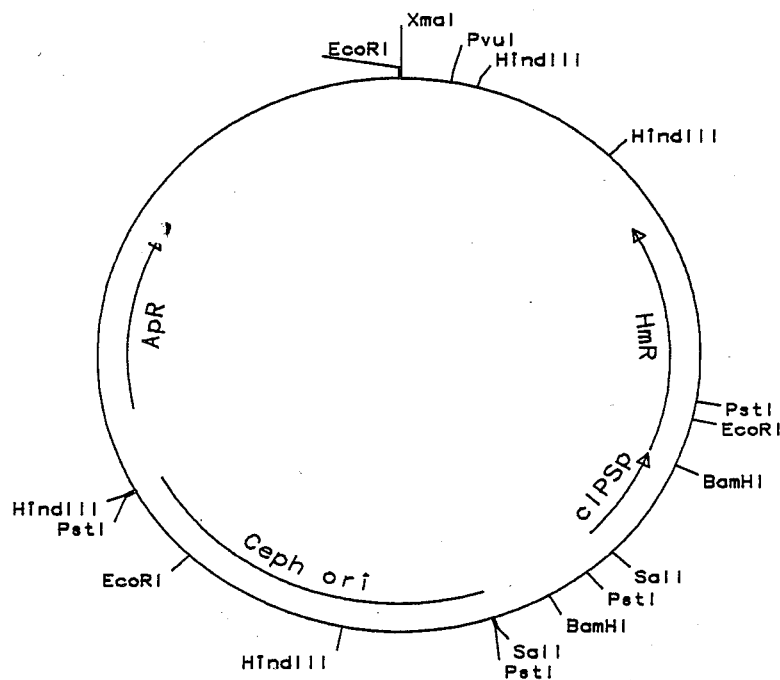
FIG. 8. A restriction site and function map of plasmid pPS21A.

Individual colonies were picked from the transformation plates, cultured, and used to prepare plasmid DNA. The plasmid DNA was analyzed by restriction enzyme analysis. Plasmid pPS21A yields restriction fragments of 7.62 kb and 0.86 kb when digested with BamHI and restriction fragments of 5.15 kb, 1.85 kb, 0.99 kb, and 0.49 kb when digested with PstI. A restriction site and function map of plasmid pPS21A is presented in FIG. 8 of the accompanying drawings.

D. Final Construction of Plasmids pPS28 and pPS29

10 About 20 μl of plasmid pPS21A DNA were dissolved in 10 μl 10X PstI reaction buffer (1.0M NaCl; 100 mM Tris-HCl, pH=7.5; 100 mM MgCl₂; and 1 mg/ml BSA) and 88 μl of H₂O. About 2 μl (150 units) of restriction enzyme PstI were added to the solution of DNA, and the reaction was incubated at 37° C. for 4 minutes, and then, the reaction was terminated by incubation at 70° C. for 10 minutes. The partially PstI-digested plasmid pPS21A DNA was loaded onto an agarose gel, and after electrophoresis and staining of the gel, the following fragments were observed: 8.5 kb (linearized plasmid); 8.0 kb; 7.5 kb; 7.0 kb; 6.6 kb; 6.1 kb; 5.2 kb; 3.3 kb; 2.3 kb; 1.9 kb; 1.5 kb; 1.0 kb; and 0.5 kb.

The ~6.6 kb and ~6.1 kb PstI restriction fragments were individually isolated in substantial accordance with the procedure of Example 2B; about 0.5 μg of each fragment were recovered.

Figure 9:
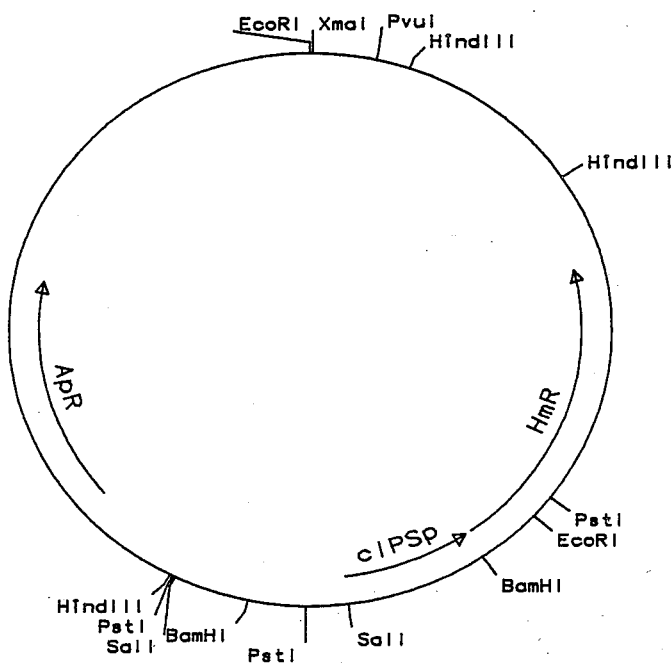
FIG. 9. A restriction site and function map of plasmid pPS28.

The ~6.6 kb PstI restriction fragment was dissolved in 3 μl 10X ligase buffer and 25 μl of H₂O. About 2 μl of T4 DNA ligase were added to the solution of DNA, and the resulting reaction was incubated at 15° C. overnight. The ligated DNA constituted the desired plasmid pPS28 DNA, which was used to transform *E. coli* K12 C600 in substantial accordance with the procedure described above. In a similar fashion, the ~6.1 kb, PstI restriction fragment was circularized by ligation to yield plasmid pPS29, which was also transformed into *E. coli* K12 C600. Restriction site and function maps of plasmids pPS28 and pPS29 are respectively presented in FIGS. 9 and 10 of the accompanying drawings.

EXAMPLE 6

Construction of Plasmids pPS45A.1, pPS45A.2, pPS45B.1, and pPS45B.2

About 20 μg of plasmid pPS29 are dissolved in 10 ∥1 10X HindIII reaction buffer (0.5M NaCl; 0.5M Tris-HCl, pH =8.0; 0.1M MgCl₂; and 1 mg/ml BSA) and 85 μl of H₂O. About 5 μl (50 units) of restriction enzyme HindIII are added to the solution of DNA, and the resulting reaction is incubated at 37° C. for two hours. The HindIII-digested plasmid pPS29 DNA is loaded onto a 1% agarose gel and electrophoresed until the ~3.2 kb, ~2.3 kb, and ~0.69 kb HindIII restriction fragments are clearly separated on the gel. The ~2.3 kb HindIII restriction fragment is isolated in substantial accordance with the procedure of Example 2B. About 5 μg of the desired ~2.3 kb HindIII restriction fragment are obtained and suspended in 10 μl of H₂O.

About 10 μg of plasmid pPS44 are dissolved in 10 μl 10X HindIII reaction buffer and 80 μl of H₂O. About 10 μl (~100 units) of restriction enzyme HindIII are added to the solution of DNA, and the resulting reaction is incubated at 37° C. for 5 minutes. The reaction is stopped by extraction with phenol, and then the reaction mixture is loaded onto a 1% agarose gel and electrophoresed until the linear, singly-cut plasmid pPS44 DNA is separated from the uncut plasmid and the products of complete digestion. The linear, singly-cut DNA is isolated from the gel in substantial accordance with the procedure of Example 2B; about 1 μg of the desired fragment is obtained and suspended in 2 μl of TE buffer.

About 2 μl of the ~2.3 kb HindIII restriction fragment of plasmid pPS29 and about 2 μl of the partially HindIII-digested plasmid pPS44 DNA are mixed with 3 μl 10X ligase buffer and 21 μl of H₂O. About 2 μl of T4 DNA ligase are added to the mixture, and the resulting ligation reaction is incubated at 16° C. for two hours. The ligated DNA constitutes the desired plasmids pPS45A.1, pPS45A.2, pPS45B.1, and pPS45B.2.

The ligated DNA is used to transform *E. coli* K12 JA221 in substantial accordance with the procedure of Example 4D. The transformed cells are plated on L-agar containing 100 μg/ml ampicillin. The ampicillin-resistant transformants are analyzed by restriction enzyme analysis of their plasmid DNA to identify the *E. coli* K12 JA221/pPS45A.1, *E. coli* K12 JA221/pPS45A.2, *E. coli* K12 JA221/pPS45B.1, and *E. coli* K12 JA221/pPS45B.2 transformants.

Plasmids pPS45A.1 and pPS45A.2 differ from plasmids pPS45B.1 and pPS45B.2 only with respect to the insertion site of the ~2.3 kb HindIII restriction fragment of plasmid pPS29. Because plasmid pPS44 comprises two HindIII restriction enzyme recognition sites, linear, singly cut, HindIII-digested plasmid pPS44 actually comprises two different types of molecules that differ with respect to where the HindIII enzyme cleaved the plasmid. Consequently, ligation of the ~2.3 kb HindIII restriction fragment of plasmid pPS29 with linear, singly-cut, HindIII-digested plasmid pPS44 produces two types of plasmids that differ with respect to the site of insertion of the ~2.3 kb fragment.

Plasmids pPS45A.1 and pPS45B.1 respectively differ from their plasmid pPS45A.2 and pPS45B.2 counterparts only with respect to the orientation of the inserted ~2.3 kb HindIII restriction fragment of plasmid pPS29. Restriction site and function maps of plasmids pPS45A.1 and pPS45B.1 are respectively presented in FIGS. 11 and 12 of the accompanying drawings.

EXAMPLE 7

Construction of Plasmids pPS42A.1, pPS42A.2, pPS42B.1, and pPS42B.2

About 10 μg of plasmid pLC2 are dissolved in 10 μl 10X HindIII reaction buffer and 80 μl of H₂O. About 10 μl (~100 units) of restriction enzyme HindIII are added to the solution of DNA, and the resulting reaction is incubated at 37° C. for 5 minutes. The reaction is stopped by extraction with phenol, and then the reaction mixture is loaded onto a 1% agarose gel and electrophoresed until the linear, singly-cut plasmid pLC2 DNA is separated from the uncut plasmid and the products of complete digestion. The linear, singly-cut DNA is isolated from the gel in substantial accordance with the procedure of Example 2B; about 1 μg of the desired fragment is obtained and suspended in 2 μl of TE buffer.

About 2 μl of the ~2.3 kb HindIII restriction fragment of plasmid pPS29 prepared in Example 6 and about 2 μl of the partially HindIII-digested plasmid pLC2 DNA are mixed with 3 μl 10X ligase buffer and 21 μl of H₂O. About 2 μl of T4 DNA ligase are added to the mixture, and the resulting ligation reaction is incubated at 16° C. for two hours. The ligated DNA constitutes the desired plasmids pPS42A.1, pPS42A.2, pPS42B.1, and pPS42B.2.

The ligated DNA is used to transform *E. coli* K12 JA221 in substantial accordance with the procedure of Example 4D. The transformed cells are plated on L-agar containing 100 μg/ml ampicillin. The ampicillin-resistant transformants are analyzed by restriction enzyme analysis of their plasmid DNA to identify the *E. coli* K12 JA221/pPS42A.1, *E. coli* K12 JA221/pPS42A.2, *E. coli* K12 JA221/pPS42B.1, and *E. coli* K12 JA221/pPS42B.2 transformants.

Plasmids pPS42A.1 and pPS42A.2 differ from plasmids pPS42B.1 and pPS42B.2 only with respect to the insertion site of the ~2.3 kb HindIII restriction fragment of plasmid pPS29. Because plasmid pLC2 comprises two HindIII restriction enzyme recognition sites, linear, singly-cut, HindIII-digested plasmid pLC2 actually comprises two different types of molecules that differ with respect to where the HindIII enzyme cleaved the plasmid. Consequently, ligation of the ~2.3 kb HindIII restriction fragment of plasmid pPS29 with linear, singly-cut, HindIII-digested plasmid pLC2 produces two types of plasmids that differ with respect to the site of insertion of the ~2.3 kb fragment.

Plasmids pPS42A.1 and pPS42B.1 respectively differ from their plasmid pPS42A.2 and pPS42B.2 counterparts only with respect to the orientation of the inserted ~2.3 kb HindIII restriction fragment of plasmid pPS29. Restriction site and function maps of plasmids pPS42A.1 and pPS42B.1 are respectively presented in FIGS. 13 and 14 of the accompanying drawings.

EXAMPLE 8

Construction of Plasmids pPS39 and pPS39.1

A. Construction of Intermediate Plasmids pPS38 and pPS38.1

(i) Preparation of BamHI-digested plasmid pUC8.

About 5 μg of plasmid pUC8 (obtained from Pharmacia P-L Biochemicals) are dissolved in 5 μl of 10X BamHI reaction buffer and 40 μl of H₂O. About 5 μl (50 units) of restriction enzyme BamHI are added to the solution of DNA, and the resulting reaction is incubated at 37° C. for two hours. The reaction is terminated by extraction with buffered phenol, followed by extraction with chloroform. The BamHI-digested plasmid pUC8 DNA is precipitated by adjusting the NaCl concentration to 0.25 M, adding 2 volumes of ethanol, and chilling at −70° C. for 10 minutes. The BamHI-digested plasmid pUC8 DNA is collected by centrifugation and resuspended in 5 μl of H₂O.

(ii) Isolation of the ~0.83 kb NcoI-BamHI restriction fragment of plasmid pLC2.

About 10 μg of plasmid pLC2 are dissolved in 5 μl of 10X BamHI buffer and 40 μl of H₂O. About 2.5 μl (25 units) each of restriction enzymes BamHI and NcoI are added to the solution of DNA, and the resulting reaction is incubated at 37° C. for two hours. The reaction mixture is then loaded onto a 1% agarose gel, and the desired ~0.83 kb NcoI-BamHI restriction fragment that comprises the transcription and translation activating sequence of the isopenicillin N synthetase gene is isolated in substantial accordance with the procedure of Example 2B. About 1 μg of the desired fragment is obtained and suspended in 5 μl of H₂O.

(iii) Preparation of the linker used in the construction of plasmid pPS38.

The single-strands of the following linker were synthesized using an automated DNA synthesizer:

About 75 picomoles of each single strand of the linker were individually dissolved in 22.5 μl of H₂O and 2.5 μl of ligase buffer. About 1 μl (10 units) of T4 DNA kinase (Bethesda Research Laboratories) was added to each solution of single-stranded DNA, and the reactions were incubated at 37° C. for 10 minutes. Following the kinase reaction, the reaction mixtures were incubated at 70° C. for 15 minutes. Then, to anneal the single-stranded DNA to form the linker, the two reaction mixtures were pooled, incubated at 65° C. for 10 minutes, incubated at room temperature for 2 hours, and then incubated at 4° C. overnight.

(iv) Final Construction of plasmids pPS38 and pPS38.1.

About 4 μl of the ~0.83 kb NcoI-BamHI restriction fragment of plasmid pLC2 are added to 10 μl of the annealed linker, 3 μl of 10X ligase buffer, 11 μl of H₂O, and 2 μl of T4 DNA ligase, and the resulting reaction is incubated at 4° C. overnight. After precipitating the ligated DNA, the DNA is resuspended in 10 μl 10X BamHI buffer and 85 μl of H₂O. About 5 μl (50 units) of restriction enzyme BamHI are added to the solution of DNA, and the resulting reaction is incubated at 37° C. for two hours. The reaction is stopped by extraction with buffered phenol, followed by extraction with chloroform, and then the DNA is precipitated several times to remove unligated linker molecules.

The DNA is resuspended in 3 μl 1 0X ligase buffer and 24 μl of H₂O. About 1 μl of the BamHI-digested plasmid pUC8 DNA and 2 μl (500 units) T4 DNA ligase are added to the mixture of DNA, and the resulting reaction is incubated at 4° C. overnight. The ligated DNA constitutes the desired plasmids pPS38 and pPS38.1.

A 50 ml culture of E. coli K12 JM109, available from Pharmacia P-L Biochemicals, in L-broth is grown to an O.D.₅₉₀ of approximately 0.5 absorbance units. The culture is chilled on ice for ten minutes, and the cells are collected by centrifugation. The cell pellet is resuspended in 25 ml of cold 100 mM CaCl₂ and incubated on ice for 25 minutes. The cells are once again pelleted by centrifugation, and the pellet is resuspended in 2.5 ml of cold 100 mM CaCl₂ and incubated on ice overnight.

Two hundred μl of this cell suspension are mixed with the ligated DNA prepared above and incubated on ice for 20 minutes. At the end of this period, the cells are placed in a water bath at 42° C. for 2 minutes and then returned to the ice for an additional 10 minutes. The cells are collected by centrifugation and resuspended in one ml of L-broth and incubated at 37° C. for 2 hours.

Aliquots of the cell mixture are plated on L-agar (L-broth with 15 grams per liter agar) plates containing 100 μg ampicillin/ml, 40 μg X-gal/ml, and 40 μg IPTG/ml. The plates are incubated at 37° C. overnight. Colonies that contain a plasmid without an insert, such as E. coli K12 JM109/pUC8, appear blue on these plates. Colonies that contain a plasmid with an insert, such as E. coli K12 JM109/pPS38, are white. Several white colonies are selected and screened by restriction analysis of their plasmid DNA for the presence of the ~0.84 kb BamHI restriction fragment that contains the isopenicillin N synthetase activating sequence. Plasmid DNA is obtained from the E. coli K12 JM109/pPS38 and E. coli K12 JM109/pPS38.1 cells in substantial accordance with the teaching of Example 2A.

B. Isolation of the ~0.84 kb BamHI Restriction Fragment of Plasmid pPS38

About 50 μg of plasmid pPS38 DNA are dissolved in 15 μl of 10X BamHI reaction buffer and 125 μl of H₂O. About 10 μl (100 units) of restriction enzyme BamHI are added to the solution of DNA, and the resulting reaction is incubated at 37° C. for two hours. The BamHI-digested plasmid pPS38 DNA is loaded onto a 1% agarose gel, and the ~0.84 kb BamHI restriction fragment that comprises the activating sequence of the isopenicillin N synthetase gene is isolated in substantial accordance with the procedure of Example 2B. About 5 μg of the desired fragment are obtained and suspended in 10 μl of H₂O.

C. Preparation of BamHI-Digested Plasmid pPS28 DNA

About 5 μg of plasmid pPS28 prepared in Example 5 are dissolved in 10 μl 10X BamHI reaction buffer and 85 μl of H₂O. About 5 μl (50 units) of restriction enzyme BamHI are added to the solution of plasmid pPS28 DNA, and the resulting reaction is incubated at 37° C. for two hours. The reaction mixture of BamHI-digested plasmid pPS28 DNA is extracted once with buffered phenol and then extracted twice with chloroform. The DNA is then precipitated, collected by centrifugation and resuspended in 10 μl of H₂O.

D. Final Construction of Plasmids pPS39 and pPS39.1

About 1 μl of the ~0.84 kb BamHI restriction fragment is added to 1 μl of the BamHI-digested plasmid pPS28 DNA, 3 μl 10X ligase buffer, 2 μl T4 DNA ligase, and 23 μl of H₂O. The resulting ligation reaction is incubated at 15° C. overnight. The ligated DNA constituted the desired plasmids pPS39 and pPS39.1.

The ligated DNA is used to transform *E. coli* K12 C600, a strain available from the American Type Culture Collection, Rockville, Md. 20852, under the accession number ATCC 33525, in substantial accordance with the procedure of Example 8A(iv). The transformed cells are plated on L-agar plates containing 100 μg/ml ampicillin, and the plates are incubated at 37° C. overnight.

Individual colonies are picked from the transformation plates, cultured, and used to prepare plasmid DNA. The plasmid DNA is analyzed by restriction enzyme analysis. Plasmids pPS39 and pPS39.1 can be distinguished from the other ligation products by digestion with restriction enzyme BamHI, for both plasmids yield ~0.84 and ~5.8 kb restriction fragments. Plasmids pPS39 and pPS39.1 can be distinguished from each other by digestion with restriction enzyme PstI, for plasmid pPS39 yields restriction fragments of ~5.15 kb, ~1.02 kb, and ~0.43 kb upon digestion with PstI, whereas plasmid pPS39.1 yields restriction fragments of ~5.15 kb, ~1.07 kb, and ~0.38 kb.

EXAMPLE 9

Construction of Plasmid pPS40

A. Construction of Plasmid pPS41

About 1 μg of plasmid pUC8 is dissolved in 2 μl 10X BamHI reaction buffer and 16 μl of H₂O. About 2 μl (20 units) of restriction enzyme BamHI are added to the solution of plasmid pUC8 DNA, and the resulting reaction is incubated at 37° C. for two hours. The BamHI-digested plasmid pUC8 DNA is extracted with phenol, and then extracted with chloroform. The BamHI-digested plasmid pUC8 DNA is precipitated, collected by centrifugation, and resuspended in 5 μl of H₂O.

About 10 μg of plasmid pLC2 are dissolved in 10 μl 1 10X BamHI reaction buffer and 80 μl of H₂O. About 5 μl (50 units) each of restriction enzymes BglII and BamHI are added to the solution of plasmid pLC2 DNA, and the resulting reaction is incubated at 37° C. for two hours. The reaction mixture is then loaded onto a 1% agarose gel and electrophoresed until the ~0.65 kb BamHI-BglII restriction fragment is separated from the other reaction products. The ~0.65 kb BamHI-BglII restriction fragment, which comprises the transcription termination and mRNA polyadenylation and processing signals of the isopenicillin N synthetase gene, is isolated in substantial accordance with the procedure of Example 2B. About 2 μg of the desired fragment are obtained and suspended in 5 μl of H₂O.

The 5 μl of BamHI-digested plasmid pUC8 are added to 2 μl of the ~0.65 kb BamHI-BglII restriction fragment of plasmid pLC2, 3 μl 10X ligase buffer, 18 μl of H₂O, and 2 μl of T4 DNA ligase. The resulting reaction is incubated at 15° C. overnight. BglII and BamHI overlaps are compatible for ligation, and once ligated, create an XhoII restriction site, but once ligated, neither BamHI nor BglII will cleave the DNA at the junction. The ligated DNA constitutes the desired plasmid pPS41 and is used to transform *E. coli* K12 RR1ΔM15, available from the NRRL under the accession number NRRL B-15440, in substantial accordance with the procedure of Example 5B(iv).

The transformed cells are plated on L-agar plates containing 100 μg/ml ampicillin, 40 μg/ml X-gal, and 40 μg/ml IPTG. Colonies that fail to produce the blue color on the transformation plates are cultured, used to prepare plasmid DNA, and the plasmid DNA is analyzed by restriction enzyme analysis to identify the *E. coli* K12 RR1ΔM15/pPS41 transformants. Because the fragment could insert in either of two orientations, only one of which creates the desired plasmid, and because the desired orientation allows the inserted DNA to be excised from plasmid pPS41 on an ~0.68 kb EcoRI-HindIII restriction fragment, the *E. coli* K12 RR1ΔM15/pPS41 transformants were identified by analysis of their plasmid DNA using restriction enzymes EcoRI and HindIII. A restriction site and function map of plasmid pPS41 is presented in FIG. 16 of the accompanying drawings.

B. Final Construction of Plasmid pPS40

About 2 μg of plasmid pPS39 are dissolved in 2 μl 10X HindIII reaction buffer and 17 μl of H₂O. About 1 μl (10 units) of restriction enzyme HindIII is added to the solution of plasmid pPS39 DNA, and the resulting reaction is incubated at 37° C. for two hours. The HindIII-digested plasmid pPS39 DNA is then precipitated, collected by centrifugation, and resuspended in 2 μl 10X EcoRI buffer (1.0M Tris-HCl, pH=7.5; 0.5M NaCl; 50 mM MgCl₂; and 1 mg/ml BSA) and 17 μl of H₂O. About 1 μl (10 units) of restriction enzyme EcoRI is added to the HindIII-digested plasmid pPS39 DNA, and the resulting reaction is incubated at 37° C. for two hours. The reaction is stopped by extraction with phenol, followed by extraction with chloroform. The EcoRI-HindIII-digested plasmid pPS39 DNA is then resuspended in 10 μl of H₂O.

About 25 μg of plasmid pPS41 are dissolved in 10 μl 10X HindIII reaction buffer and 85 μl of H₂O. About 5 μl (50 units) of restriction enzyme HindIII are added to the solution of DNA, and the resulting reaction is incubated at 37° C. for two hours. The HindIII-digested plasmid pPS41 DNA is then precipitated, collected by centrifugation, and resuspended in 10 μl 10X EcoRI buffer and 85 μl of H₂O. About 5 μl (50 units) of restriction enzyme EcoRI are added to the solution of DNA, and the resulting reaction is incubated at 37° C. for 2 hours.

The EcoRI-HindIII-digested plasmid pPS41 DNA is loaded onto a 1% agarose gel and electrophoresed until the ~0.68 kb EcoRI-HindIII restriction fragment that comprises the transcription termination and mRNA polyadenylation and processing signals of the isopenicillin N synthetase gene of *Penicillium chrysogenum* is clearly separated from the other reaction products. The ~0.68 kb restriction fragment is then isolated and purified in substantial accordance with the procedure of Example 2B. About 2 μg of the desired fragment are obtained and suspended in 5 μl of H₂O.

About 5 μl of the HindIII-EcoRI-digested plasmid pPS39 DNA are added to 3 μl of the ~0.68 kb EcoRI-HindIII restriction fragment of plasmid pPS41. About 3 μl of 10X ligase buffer, 17 μl of H₂O, and 2 μl of T4 DNA ligase are then added to the mixture of DNA, and the resulting ligation reaction is incubated at 16° C. for two hours.

The ligated DNA constitutes the desired plasmid pPS40. The ligated DNA is used to transform *E. coli* K12 JA221 in substantial accordance with the procedure of Example 4D. The *E. coli* K12 JA221/pPS40 transformants are identified by their ampicillin-resistant phenotype and by restriction enzyme analysis of their plasmid DNA. Plasmid pPS40 is identical to plasmid pPS39, except that plasmid pPS40 comprises the ~0.68 kb EcoRI-HindIII restriction fragment of plasmid pPS41 where plasmid pPS39 has an EcoRI-HindIII restriction fragment ~0.356 kb in size and a HindIII restriction fragment about ~0.685 kb in size. A restriction site and function map of plasmid pPS40 is presented in FIG. 17 of the accompanying drawings.

EXAMPLE 10

Genetic Transformation of *Cephalosporium acremonium* and *Penicillium chrysogenum*.

The transformation procedure set forth below is disclosed and claimed in U.S. patent application Ser. No. 654,919, filed Sept. 27, 1984. This procedure is specifically designed for transformation of *Cephalosporium acremonium* with vectors that comprise a hygromycin resistance-conferring gene. The procedure is also applicable to *Penicillium chrysogenum* and can be used with vectors that do not comprise a hygromycin resistance-conferring gene merely by modifying the procedure to eliminate the hygromycin overlay of the transformation plates.

Penicillium is much more resistant to hygromycin than Cephalosporium. Consequently, high levels of hygromycin are needed if a Penicillium transformant is to be identified via its hygromycin-resistant phenotype. Alternatively, because the natural resistance of Penicillium to hygromycin is believed to be due to the difficulty with which hygromycin crosses the Penicillium host cell membrane, permeabilizing agents such as DMSO or alamethicin can be used in the transformation plates. An especially preferred permeabilizing agent useful for the purpose of sensitizing *Penicillium chrysogenum* to hygromycin is the nonapeptide produced upon ficin cleavage of polymixin B. Furthermore, through use of mutagenizing agents, mutant *Penicillium chrysogenum* strains that are sensitive to low levels of hygromycin can be isolated and used as hosts for the hygromycin resistance-conferring vectors of the present invention.

If the vector does not contain a selectable marker that functions in *Penicillium chrysoqenum* or *Cephalosporium acremonium*, transformants can still be identified by screening the colonies that arise on the regeneration plates for the presence of the transforming DNA. Such screening methods include the use of hybridization and restriction enzyme analysis. Plasmids pLC2 and pPS44 do not comprise selectable markers that function in *Penicillium chrysoqenum* or *Cephalosporium acremonium*, so plasmid pLC2 or pPS44 transformants of *P. chrysogenum* or *C. acremonium* obtained by the following procedure must be identified by analysis of their DNA. Plasmids pPS39, pPS40, pPS42A.1, pPS42B.1, pPS42A.2, pPS42B.2, pPS45A.1, pPS45B.1, pPS45A.2, and pPS45B.2 do comprise a selectable marker, for hygromycin resistance, and transformants of *P. chrysogenum* or *C. acremonium* obtained by the following procedure using these plasmids can be identified both by their hygromycin-resistant phenotype and by analysis of their DNA.

A. *Cephalosporium acremonium* Strains

The preferred Cephalosporium strain for transformation is obtained from the American Type Culture Collection, Rockville, Md., under the accession number ATCC 11550. Other Cephalosporium strains or any commercial strains derived from ATCC 11550 by mutation, selection, or genetic breeding for the purpose of improved production of cephalosporin C are also suitable for use in preparing transformants with the vectors and plasmids of the present invention.

B. Preparation of Inoculum for Cell Culture

To genetically transform *Cephalosporium acremonium* cells efficiently, it is necessary to remove the cell walls to form stable protoplasts. In the preparation of such protoplasts, it is highly advantageous to begin with a uniform inoculum. Otherwise, preparation of cells in culture is not reproducible and time is lost by attempts to prepare *C. acremonium* protoplasts from unsuitable or inadequate amounts of cells.

C. Preparation of Uniform Inoculum for Cell Culture

An ampoule of spores (approximately $10^9$ conidia in 1.5 ml of preservation menstrum: 5% lactose, 10% glycerol, and 0.1% Tween 80), either lyophilized or taken from liquid nitrogen storage and thawed at room temperature, are diluted in 5 ml of sterile saline. About 0.1 ml of this suspension is used to inoculate each of approximately 50 slants containing 20 ml of Trypticase ®-Soy Agar (BBL TM, Division of Becton, Dickinson & Company, Cockeysville, Md. 21030) medium. Before inoculation, the medium is allowed to dry until surface moisture is no longer visible. Inoculated slants are incubated for about four days at 25° C. About 10 ml of preservation menstrum are added to the mycelial growth which covers the surface of the medium in each slant. The slants are vortexed to suspend the conidia, and the conidial suspension from each slant is pooled and 10 ml aliquots frozen at −80° C. The frozen conidial suspension slowly loses viability and should not be used after about three months of storage at −80° C.

D. Growth of Cells for Preparation of Protoplasts

Approximately 106 ml of aqueous medium 500 ml shake flask are inoculated with cells from the 10 ml of frozen conidial suspension prepared in Example 10C. Cells are obtained by centrifugation (10 min×2600 rpm), and then directly suspended in the aqueous culture medium*. Decantation of the supernatant is necessary prior to suspension, because the lactose and glycerol adversely affect the growth of cells. The flask containing the suspended cells is placed on a gyrotory water bath shaker and incubated at 29°–30° C. for 24 hours at 285 rpm with a 1 inch throw. The recommended temperature of 29°–30° C. in the culturing step is especially preferred for preparing transformable protoplasts, but lower temperatures of about 25° C. are also suitable. Those familiar with the art will recognize that the 29°–30° C. is different from the temperature (25° C.) preferred for culturing *Cephalosporium acremonium* for purposes of antibiotic production.

*Aqueous culture medium was prepared as follows: one hundred ml of solution A are dispensed into a 500 ml shake flask; the flask is covered with a commercial closure and is autoclaved at 121° C. for 20 minutes. Two ml of solution B and 4 ml of solution C are then added to solution A to prepare the aqueous culture medium.
Solution A: Sucrose, 36 g/L; L-asparagine, 7.5 g/L; $KH_2PO_4$, 15 g/L; $K_2HPO_4$, 21 g/L; $Na_2SO_4$,0.75 g/L, $MgSO_4 \cdot 7H_2O$; 0.18 g/L; $CaCl_2$,0.6 g/L; salts solution, 1 ml/L; natural pH. Salts solution: $Fe(NH_4)(SO_4)_2 \cdot 6H_2O$, 15 g/L; $MnSO_4 \cdot 4H_2O$, 3 g/L: $ZnSO_4 \cdot 7H_2O$, 3 g/L; $CuSO_4 \cdot 5H_2O$, 0.8 g/L).
Solution B: Glucose, 108 g/L (autoclaved at 121° C., 30 minutes)
Solution C: Sucrose, 25 g/L; corn steep liquor (4% w/v nitrogen), 12.5 ml; ammonium acetate, 5.5 g/L; $CaCO_3$, 5 g/L; pH adjusted to 6.5 with KOH; and autoclaved at 121° C. for 20 minutes.

E. Preparation of Cephalosporium Protoplasts

Cells from a 24 hour culture are harvested by suction filtration (Whatman #1 paper in a Buchner funnel) and suspended in McIlvaine's Buffer, pH=7.1, (0.1M citric acid and 0.2M dibasic sodium phosphate) to which dithiothreitol has been added to a concentration of 0.01M. Sufficient buffer is added to obtain a final cell concentration of 1 g (weighed after suction filtration) of cell mass per 20 ml of buffer. The cell suspension is placed on a gyrotory water bath shaker in a 50 ml shake flask and incubated at 29°-30° C. for 90 minutes at 140 rpm with 1 inch throw. Dithiothreitol-treated cells are washed with water and then resuspended in enzyme solution (25 mg/ml of beta-glucuronidase from Sigma Chemical Company, in McIlvaine's buffer, pH=6.35, and supplemented with 0.8 M NaCl and 0.02 M MgSO$_4$). The final cell concentration is 1 g of treated cell mass per 10 ml of enzyme solution. The cell suspension is then placed on a gyrotory water bath shaker at 29°-30° C. for 3 hours at 120 rpm with a 1 inch throw. The suspension of protoplasts is diluted with 4 volumes of washing solution (0.8 M NaCl and 0.02 M MgSO$_4$) and then gravity filtered through two layers of paper towels. The filtrate containing the protoplasts is centrifuged at room temperature for 5 minutes at 2600 rpm. The supernatant is decanted, and the pellet of protoplasts is suspended in 10 ml of washing solution. After repeating the washing procedure twice, the protoplasts are resuspended in sufficient 0.8 M NaCl to achieve a concentration of 2 to 3×10$^8$ protoplasts per ml, by hemacytometer count.

F. Transformation Procedure

For each plasmid to be transformed, a 1 ml suspension of Cephalosporium protoplasts (2 to 3×10$^8$ per ml) in 0.8M NaCl is added to 0.005 ml of freshly distilled DMSO and then made 80 mM in CaCl$_2$. About 20 µg of transforming plasmid and polyethylene glycol 4000 (Baker, >20% w/v in water) are added to the suspension of protoplasts to achieve a mixture with a volume of 10 ml. The mixture is incubated for 10 minutes at room temperature and then centrifuged at 700 rpm for 5 minutes, which is followed by a 2500 rpm centrifugation for 10 minutes. The pellet of protoplasts is suspended in 1 ml of 0.8 M NaCl. Aliquots (0.1 ml) are delivered to the surface of Trypticase-Soy Agar medium (BBL) that has been enriched with 10.8% sucrose to osmotically stabilize the protoplasts.

After the petri plates are incubated at 15° C. for 24 hours, 4 ml of liquified agar (0.41% w/v, at 42° C.) containing 0.8M sodium chloride and sufficient hygromycin to achieve a final concentration of 100 µg/ml are added to each petri dish. After the overlay has solidified, the petri plates are then incubated at 25° C. in a humidified chamber. Although transformant colonies of sufficient size to subculture are present about 5 days after transformation, slower growing transformants may take as long as 60 days to achieve a suitable size for subculture. Abortive transformants are easily distinguished from stable transformants, because abortive transformants fail to grow upon subculture to fresh medium containing 100 µg/ml of hygromycin.

We claim:

1. An isolated DNA compound that comprises a DNA sequence that encodes the isopenicillin N synthetase activity of *Penicillium chrysogenum*.

2. The DNA compound of claim 1 wherein the isopenicillin N synthetase activity comprises the amino acid sequence, from amino to carboxy terminus:

```
MET ALA SER THR PRO LYS ALA ASN VAL PRO LYS ILE ASP VAL SER PRO
LEU PHE GLY ASP ASN MET GLU GLU LYS MET LYS VAL ALA ARG ALA ILE
ASP ALA ALA SER ARG ASP THR GLY PHE PHE TYR ALA VAL ASN HIS GLY
VAL ASP VAL LYS ARG LEU SER ASN LYS THR ARG GLU PHE HIS PHE SER
ILE THR ASP GLU GLU LYS TRP ASP LEU ALA ILE ARG ALA TYR ASN LYS
GLU HIS GLN ASP GLN ILE ARG ALA GLY TYR TYR LEU SER ILE PRO GLU
LYS LYS ALA VAL GLU SER PHE CYS TYR LEU ASN PRO ASN PHE LYS PRO
ASP HIS PRO LEU ILE GLN SER LYS THR PRO THR HIS GLU VAL ASN VAL
TRP PRO ASP GLU LYS LYS HIS PRO GLY PHE ARG GLU PHE ALA GLU GLN
TYR TYR TRP ASP VAL PHE GLY LEU SER SER ALA LEU LEU ARG GLY TYR
ALA LEU ALA LEU GLY LYS GLU GLU ASP PHE PHE SER ARG HIS PHE LYS
LYS GLU ASP ALA LEU SER SER VAL VAL LEU ILE ARG TYR PRO TYR LEU
ASN PRO ILE PRO PRO ALA ALA ILE LYS THR ALA GLU ASP GLY THR LYS
LEU SER PHE GLU TRP HIS GLU ASP VAL SER LEU ILE THR VAL LEU TYR
GLN SER ASP VAL ALA ASN LEU GLN VAL GLU MET PRO GLN GLY TYR LEU
ASP ILE GLU ALA ASP ASP ASN ALA TYR LEU VAL ASN CYS GLY SER TYR
MET ALA HIS ILE THR ASN ASN TYR TYR PRO ALA PRO ILE HIS ARG VAL
LYS TRP VAL ASN GLU GLU ARG GLN SER LEU PRO PHE PHE VAL ASN LEU
GLY PHE ASN ASP THR VAL GLN PRO TRP ASP PRO SER LYS GLU ASP GLY
LYS THR ASP GLN ARG PRO ILE SER TYR GLY ASP TYR LEU GLN ASN GLY
LEU VAL SER LEU ILE ASN LYS ASN GLY GLN THR
``` wherein ALA is an Alanine residue, ARG is an Arginine residue, ASN is an Asparagine residue, ASP is an Aspartic Acid residue, CYS is a Cysteine residue, GLN is a Glutamine residue, GLU is a Glutamic Acid residue, GLY is a Glycine residue HIS is a Histidine residue, ILE is an Isoleucine residue, LEU is a Leucine residue, LYS is a Lysine residue, MET is a Methionine residue, PHE is a Phenylalanine residue, PRO is a Proline residue, SER is a Serine residue, THR is a Threonine residue, TRP is a Tryptophan residue, TYR is a Tyrosine residue, and VAL is a Valine residue.

3. The isopenicillin N synthetase encoded by the DNA compound of claim 2.

4. The DNA compound of claim 2 wherein the sequence of the coding strand is:

```
5'- ATG GCT TCC ACC CCC AAG GCC AAT GTC CCC AAG ATC GAC GTG TCG CCC
    CTG TTC GGC GAC AAT ATG GAG GAG AAG ATG AAG GTT GCC CGC GCG ATT
    GAC GCT GCC TCG CGC GAC ACC GGC TTC TTC TAC GCG GTC AAC CAC GGT
    GTG GAT GTG AAG CGA CTC TCG AAC AAG ACC AGG GAG TTC CAC TTT TCT
    ATC ACA GAC GAA GAG AAG TGG GAC CTC GCG ATT CGC GCC TAC AAC AAG
    GAG CAC CAG GAC CAG ATC CGT GCC GGA TAC TAC CTG TCC ATT CCG GAG
    AAA AAG GCC GTG GAA TCC TTC TGC TAC CTG AAC CCC AAC TTC AAG CCC
    GAC CAC CCT CTC ATC CAG TCG AAG ACT CCC ACT CAC GAG GTC AAC GTG
```

```
            -continued
TGG CCG GAC GAG AAG AAG CAT CCG GGC TTC CGC GAG TTC GCC GAG CAA
TAC TAC TGG GAT GTG TTC GGG CTC TCG TCT GCC TTG CTG CGA GGC TAT
GCT CTG GCG CTG GGC AAG GAG GAG GAC TTC TTT AGC CGC CAC TTC AAG
AAG GAA GAC GCG CTC TCC TCG GTT GTT CTG ATT CGT TAC CCG TAC CTG
AAC CCC ATC CCA CCT GCC GCC ATT AAG ACG GCG GAG GAC GGC ACC AAA
TTG AGT TTC GAA TGG CAT GAG GAC GTG TCG CTC ATT ACC GTC CTG TAC
CAG TCA GAC GTG GCG AAC CTG CAG GTG GAG ATG CCC CAG GGT TAC CTC
GAT ATC GAG GCG GAC GAC AAC GCC TAC CTG GTC AAT TGC GGC AGC TAC
ATG GCA CAC ATC ACC AAC AAC TAC TAC CCC GCT CCC ATC CAC CGG GTC
AAG TGG GTG AAC GAG GAG CGC CAA TCC CTC CCG TTC TTC GTC AAT CTG
GGA TTT AAT GAT ACC GTC CAG CCG TGG GAT CCT AGC AAG GAA GAC GGC
AAG ACC GAT CAG CGG CCA ATC TCG TAC GGC GAC TAT CTG CAG AAC GGA
TTA GTT AGT CTA ATC AAC AAG AAC GGC CAG ACA-3'
``` wherein A is deoxyadenyl, G is deoxyguanyl, C is deoxycytidyl, and T is thymidyl.

5. A recombinant DNA vector that comprises the DNA compound of claim 1.

6. A recombinant DNA vector that comprises the DNA compound of claim 2.

7. A recombinant DNA vector that comprises the DNA compound of claim 4.

8. The recombinant DNA vector of claim 7 that is a plasmid.

9. The plasmid of claim 8 that is plasmid pLC2.

10. The plasmid of claim 8 that is plasmid pLC3.

11. The plasmid of claim 8 that is plasmid pPS44.

12. The plasmid of claim 8 that is plasmid pPS45A.1.

13. The plasmid of claim 8 that is plasmid pPS45A.2.

14. The plasmid of claim 8 that is plasmid pPS45B.1.

15. The plasmid of claim 8 that is plasmid pPS45B.2.

16. The plasmid of claim 8 that is plasmid pPS42A.1.

17. The plasmid of claim 8 that is plasmid pPS42A.2.

18. The plasmid of claim 8 that is plasmid pPS42B.1.

19. The plasmid of claim 8 that is plasmid pPS42B.2.

20. A host cell transformed with a plasmid of claim 8.

21. The transformed host cell of claim 20 that is *E. coli* K12.

22. The transformed host cell of claim 21 that is *E. coli* K12 RV308/pLC3.

23. The transformed host cell of claim 21 that is *E. coli* K12 JM109/pLC2.

24. The transformed host cell of claim 20 that is *Penicillium chrysogenum*.

25. The *Penicillium chrysogenum* host cell of claim 24 transformed with a vector selected from the group consisting of plasmids pLC2, pPS44, pPS45A.1, pPS45A.2, pPS45B.1, pPS45B.2, pPS42A.1, pPS42A.2, pPS42B.1, and pPS42B.2.

26. The transformed host cell of claim 20 that is *Cephalosporium acremonium*.

27. The *Cephalosporium acremonium* host cell of claim 26 transformed with a vector selected from the group consisting of pLC2, pPS44, pPS45A.1, pPS45A.2, pPS45B.1, pPS45B.2, pPS42A.1, pPS42A.2, pPS42B.1, and pPS42B.2.

28. An isolated DNA compound that comprises the transcription and translation activating sequence of the isopenicillin N synthetase gene of *Penicillium chrysogenum*.

29. The DNA compound of claim 28 that is the ~0.83 kb BamHI-NcoI restriction fragment of plasmid pLC2.

30. A recombinant DNA vector that comprises the DNA compound of claim 28.

31. The recombinant DNA vector of claim 30 that is a plasmid.

32. The plasmid of claim 31 that is plasmid pPS38.

33. The plasmid of claim 31 that is plasmid pPS38.1.

34. The plasmid of claim 31 that is plasmid pPS39.

35. The plasmid of claim 31 that is plasmid pPS40.

36. A host cell transformed with a vector of claim 31.

37. The transformed host cell of claim 36 that is *Penicillium chrysogenum*.

38. The *Penicillium chrysogenum* host cell of claim 37 transformed with a vector selected from the group consisting of plasmids pPS39 and pPS40.

39. The transformed host cell of claim 36 that is *Cephalosporium acremonium*.

40. The *Cephalosporium acremonium* host cell of claim 39 transformed with a vector selected from the group consisting of plasmids pPS39 and pPS40.

41. An isolated DNA compound that comprises the transcription termination and mRNA polyadenylation and processing signals of the isopenicillin N synthetase gene of *Penicillium chrysogenum*.

42. The DNA compound of claim 41 that is the ~0.65 kb BamHI-BglII restriction fragment of plasmid pLC2.

43. A recombinant DNA vector that comprises the DNA compound of claim 41.

44. The recombinant DNA vector of claim 43 that is a plasmid.

45. The plasmid of claim 44 that is plasmid pPS41.

46. A host cell transformed with a plasmid of claim 44.

47. The transformed host cell of claim 46 that is selected from the group consisting of *Penicillium chrysogenum* and *Cephalosporium acremonium*.

48. A method of producing isopenicillin N synthetase in a recombinant host cell that comprises:
   (1) transforming said host cell with a recombinant vector that comprises:
      (a) a transcription and translation activating sequence; and
      (b) the DNA compound of claim 1 positioned for expression from said activating sequence; and
   (2) culturing said host cell transformed in step (1) under conditions that allow for gene expression.

49. A method of producing isopenicillin N synthetase in a recombinant host cell that comprises:
   (1) transforming said host cell with a recombinant vector that comprises:
      (a) a transcription and translation activating sequence; and
      (b) the DNA compound of claim 2 positioned for expression from said activating sequence; and
   (2) culturing said host cell transformed in step (1) under conditions that allow for gene expression.

50. The method of claim 48 wherein said host cell is *E. coli*.

51. The method of claim 48 wherein said host cell is *Penicillium chrysogenum*.

52. The method of claim 48 wherein said host cell is *Cephalosporium acremonium*.

53. The method of claim 48 wherein said host cell is *Streptomyces*.

54. A method of producing a functional polypeptide in a recombinant host cell that comprises:
(1) transforming said host cell with a recombinant vector that comprises:
 (a) the transcription and translation activating sequence of claim 28; and
 (b) a DNA compound that encodes said functional polypeptide and that is positioned for expression from said activating sequence; and
(2) culturing said host cell transformed in step (1) under conditions that allow for gene expression.

55. The method of claim 54 wherein said host cell is *Penicillium chrysogenum*.

56. The method of claim 54 wherein said host cell is *Cephalosporium acremonium*.

57. The method of claim 54 wherein said functional polypeptide is an antibiotic biosynthetic enzyme.

58. The method of claim 54 wherein said functional polypeptide is an antibiotic resistance-conferring enzyme.

59. The method of claim 57 wherein said antibiotic biosynthetic enzyme is isopenicillin N synthetase.

60. The method of claim 58 wherein said antibiotic resistance-conferring enzyme is hygromycin phosphotransferase.

61. A plasmid selected from the group consisting of plasmids pIT344 and pIT344.1.

62. The plasmid of claim 8 that is plasmid pIT345.

63. The plasmid of claim 8 that is plasmid pIT345.1.

64. The transformed host cell of claim 21 that is *E. coli* K12/pIT345.

65. The transformed host cell of claim 21 that is *E. coli* K12/pIT345.1.

* * * * *